(12) United States Patent
Balint et al.

(10) Patent No.: US 7,335,478 B2
(45) Date of Patent: Feb. 26, 2008

(54) REACTIVATION-BASED MOLECULAR INTERACTION SENSORS

(75) Inventors: Robert F. Balint, Palo Alto, CA (US); Jeng-Horng Her, San Jose, CA (US)

(73) Assignee: KaloBios Pharmaceuticals, Inc., Palo Alto, CA (US)

( * ) Notice: Subject to any disclaimer, the term of this patent is extended or adjusted under 35 U.S.C. 154(b) by 604 days.

(21) Appl. No.: 10/208,730

(22) Filed: Jul. 29, 2002

(65) Prior Publication Data

US 2003/0198971 A1 Oct. 23, 2003

Related U.S. Application Data

(60) Provisional application No. 60/379,718, filed on May 10, 2002, provisional application No. 60/373,802, filed on Apr. 18, 2002, provisional application No. 60/373,765, filed on Apr. 18, 2002.

(51) Int. Cl.
G01N 33/53 (2006.01)

(52) U.S. Cl. ................. 435/7.1; 435/7.92; 435/6; 436/86; 436/164

(58) Field of Classification Search ............. 435/7.1, 435/7.92, 6, 333; 436/86, 164
See application file for complete search history.

(56) References Cited

U.S. PATENT DOCUMENTS

| 5,503,977 | A * | 4/1996 | Johnsson et al. .............. 435/6 |
| 5,925,523 | A | 7/1999 | Dove et al. |
| 6,057,101 | A | 5/2000 | Nandabalan et al. |
| 6,270,964 | B1 | 8/2001 | Michnick et al. |
| 6,294,330 | B1 | 9/2001 | Michnick et al. |

(Continued)

FOREIGN PATENT DOCUMENTS

WO    WO98/44350 A1    10/1998

(Continued)

OTHER PUBLICATIONS

Petrosino, Joseph et al.; "Contributions of aspartate 49 and phenylalanine 142 residues of a tight binding inhibitory protein of β-lactamases"; The Journal of Biological Chemistry; Jan. 22, 1999, pp. 2394-2400; vol. 274, No. 4; The American Society of Biochemistry and Molecular Biology, Inc.; USA.

(Continued)

Primary Examiner—Long V. Le
Assistant Examiner—Jacob Cheu
(74) Attorney, Agent, or Firm—Townsend and Townsend and Crew LLP

(57) ABSTRACT

This invention provides methods and systems for linking the functional activation of a responder molecule to the interaction of two or more binding ensemble members of interest either in vitro or in vivo, and thereby producing a signal, phenotype, or other functional output in response to the interaction of the binding ensemble members. The systems comprise a responder, an inhibitor of the responder, and an inhibitor of the inhibitor, or "reactivator" of the responder, and interacting components. Two binding ensemble members are complexed to the other components of the system in such a way that interaction of the binding ensemble members, either directly or via additional ensemble members, causes a shift in the equilibrium of inhibitor binding from the responder to the reactivator, thereby functionally activating the responder.

29 Claims, 14 Drawing Sheets

U.S. PATENT DOCUMENTS

| | | | |
|---|---|---|---|
| 6,342,345 | B1 | 1/2002 | Blau et al. |
| 6,974,684 | B2 | 12/2005 | Anderson et al. |
| 2002/0155502 | A1 | 10/2002 | Balint et al. |
| 2003/0054413 | A1* | 3/2003 | Kumaraswamy et al. .... 435/7.5 |
| 2003/0157579 | A1 | 8/2003 | Balint et al. |
| 2003/0175836 | A1 | 9/2003 | Blau et al. |
| 2004/0132066 | A1 | 7/2004 | Balint et al. |
| 2005/0142623 | A1 | 6/2005 | Yanagawa et al. |

FOREIGN PATENT DOCUMENTS

| | | |
|---|---|---|
| WO | WO 00/71702 A1 | 11/2000 |
| WO | WO 01/51629 A2 | 7/2001 |

OTHER PUBLICATIONS

Strynadka, Natalie C. J. et al.; "Structural and kinetic characterization of a β-lactamase-inhibitor protein"; *Nature*; Apr. 14, 1994; pp. 657-660; vol. 368.

Chen, L., et al., "Highly sensitive biological and chemical sensors based on reversible fluorescence quenching in a conjugated polymer," *PNAS*, Oct. 26, 1999, vol. 96, No. 22, 12287-12292.

Johnsson, N., et al., "Split ubiquitin as a sensor of protein interactions in vivo," *Proc. Natl. Acad. Sci. USA*, Oct. 1994, vol. 91, pp. 10340-10344.

Rossi, F., et al., "Monitoring protein-protein interactions in intact eukaryotic cells by β-galactosidase complementation," *Proc. Natl. Acad. Sci. USA*, Aug. 1997, vol. 94, pp. 3405-3410.

Wehrman, Tom, et al., "Protein-protein interactions monitored in mammalian cells via complementation of β-lactamase enzyme fragments," *PNAS* (Mar. 19, 2002) 99(6):3469-3474.

Wigley, W. Christian, et al., "Protein solubility and folding monitored in vivo by structural complementation of a genetic marker protein," *Nature Biotechnology* (Feb. 2001) 19: 131-136.

* cited by examiner

A.

B.

A.

B.

REACTIVATION-BASED MOLECULAR INTERACTION SENSORS

CROSS-REFERENCES TO RELATED APPLICATIONS

This application claims the benefit of U.S. Provisional Application Nos. 60/373,765, filed Apr. 18, 2002; 60/373,802, filed Apr. 18, 2002; and 60/379,718, filed May 10, 2002, each of which applications is incorporated by reference herein.

BACKGROUND OF THE INVENTION

Current methods of detecting interactions of binding pair partners by activation of a responder protein rely primarily on the complementation of inactive responder fragments or subunits to reconstitute the active responder. Typically, molecules of interest, e.g., members of binding pairs, are fused to the fragments or subunits, which do not complement on their own, but can do so when brought together by interaction of the binding pair members. For example, the yeast two-hybrid system has been used to identify cDNA translation products that interact with a protein of interest. This system uses fragments of a gene transcription factor fused to the protein of interest and candidate cDNA products, such that when an interaction occurs inside yeast cells, the fragments complement to activate expression of a responder gene. Another system, based on complementation of fragments of the enzyme dihydrofolate reductase (DHFR), has been used to monitor the interaction of proteins both inside and on the surface of mammalian cells using a fluorescent inhibitor of the enzyme to detect interactions stoichiometrically. Fragment complementation systems of the enzyme β-lactamase have also been used for detection of protein-protein interactions in mammalian cells using a fluorogenic substrate for signal amplification, and in the periplasmic space of gram-negative bacteria using enzyme-conferred antibiotic resistance to select interacting pairs (see, e.g., co-pending U.S. patent application Ser. No. 09/526,106). Similarly, low-affinity truncations of subunits of the enzyme β-galactosidase have been used to monitor protein-protein interactions both inside and on the surface of mammalian cells using a fluorogenic substrate of the enzyme.

In spite of their utility, all of the forgoing systems have drawbacks related to two fundamental properties of such systems. First, unnatural fragments of natural proteins tend to be inherently unstable because they necessarily expose hydrophobic structures, which are normally sequestered in the interior of the protein, to the aqueous environment. Likewise, mutant subunits tend to be unstable when assembly of the complex is delayed or prevented. As a result, the usefulness of such systems for the discovery of natural interactors, for example, in libraries of expressed sequences or of antigen-specific antibodies in repertoire libraries, is seriously compromised because many of the fusions comprising the unstable fragments or subunits may not be stable enough to facilitate detectable interactions. Furthermore, the inherent instability of the components makes them poorly suited for therapeutic use or for in vitro applications, such as clinical diagnostics.

The second compromising property of the foregoing systems is that natural proteins reconstituted from fragments or low-affinity mutant subunits typically have specific activities that are orders of magnitude lower than those of the intact protein. Insofar as the specific activity of the responder is the principal determinant of the sensitivity of the system, the latter will be similarly affected.

The current invention circumvents many of these limitations by using intact, natural proteins as responders, inhibitors, and reactivators. Thus, the full activity of the responder is available for more sensitive detection of the molecule or interaction of interest, and the stable components make these systems suitable for many applications for which fragment or subunit complementation systems are not practical. For example, analyte-activated systems in which responder activation is directly coupled to interaction with a target analyte can form the basis of sensitive and convenient analyte assays. Such assays are homogeneous, requiring no manipulations other than mixing a clinical specimen with the components of a system of the invention, which include responder, inhibitor, and reactivator fused to molecules that bind the analyte, and in so doing shift the equilibrium of inhibitor binding from the responder to the reactivator, thereby activating the responder, such that the responder output is directly proportional to the absolute amount of analyte in the specimen.

BRIEF SUMMARY OF THE INVENTION

The current invention provides methods and systems for detecting a binding interaction. The systems comprise the following components: a responder protein, an inhibitor of the responder, a reactivator and binding ensemble members.

Thus, in one aspect, the invention provides a responder complex comprising a responder molecule, a reactivator, and a binding ensemble member, which in some embodiments is a member of a plurality of candidate binding ensemble members. The components of the responder complex may be arranged in various configurations. In one configuration, the binding ensemble is linked to the responder molecule and the inhibitor is linked to the responder molecule. In another configuration, the responder molecule is linked to the member of the binding ensemble, and the inhibitor is linked to the member of the binding ensemble. In another configuration, the responder molecule is linked to the inhibitor and the binding ensemble member is linked to the inhibitor. Any of the linkages may be covalent or non-covalent. In some embodiments, the covalent linkages further comprise a linker. Often, the components of the responder complex are all linked by covalent linkages. In other embodiments, they are all linked by non-covalent linkages. In alternative embodiments, one linkage is non-covalent and the other is covalent.

In another aspect the invention provides a reactivator complex comprising a reactivator molecule and a binding ensemble member, which may be a member of a plurality of candidate binding ensemble members. The reactivator and binding ensemble member may be linked either covalently or non covalently. The covalent linkage may further comprise a linker.

The invention also provides host cells, nucleic acids and expression vectors that encode responder and reactivator complexes in which the components are covalently linked.

In another aspect the invention provides systems comprising a responder complex and a reactivator complex, wherein the responder complex comprises a first member of a binding ensemble and the reactivator complex comprises a second member of the binding ensemble. Any of the responder complex configurations may be used in the systems. Further, the components of the reactivator and responder complexes may be covalently or non-covalently linked.

In some embodiments, the first member of the binding ensemble is a member of a plurality of candidate binding ensemble members. In another embodiment, the second member of the binding ensemble is a member of a plurality of candidate binding ensemble members. In other embodiments, the method further comprises a third member of the binding ensemble, wherein the first member of the binding ensemble and the second member of the binding ensemble interact with the third member of the binding ensemble. The third member may also be a member of a plurality of candidate binding ensemble members. In additional embodiments, all three binding ensemble members are members of a plurality of candidate binding ensemble members.

In another aspect, the invention provides a method for detecting an interaction of binding ensemble members, comprising the steps of: providing a responder complex comprising a responder molecule, an inhibitor, and a first member of a binding ensemble; providing a reactivator complex comprising a reactivator molecule and a second member of the binding ensemble; combining the responder complex and the reactivator complex; and detecting an activity of the responder molecule, thereby detecting the interaction of the first and the second binding ensemble members. Any of the responder complex configurations may be used. Further, the components in the responder and reactivator complexes may be covalently or non-covalently linked. In some embodiments, the method comprises a step of providing a third member of the binding ensemble. The first member of the binding ensemble may be a member of a plurality of candidate binding ensemble members. In other embodiments, the second member of the binding ensemble is a member of a plurality of candidate binding ensemble members. The third member may also be a member of a plurality of candidate binding ensemble members. In some embodiments, all three binding pair members or members of a plurality of candidate binding ensemble members.

In another aspect, the invention provides a method of interaction mapping, comprising the steps of: providing a plurality of responder complexes comprising a responder molecule, an inhibitor and a binding ensemble member; providing a plurality of reactivator complexes comprising a plurality of candidate binding ensemble members, wherein each candidate binding ensemble member is individually linked to a reactivator molecule; individually combining at least one member of the plurality of reactivator complexes with a responder complex; and detecting an activity of the responder molecule, thereby detecting the interaction of the binding ensemble member with at least one of the plurality of candidate binding ensemble members. The method may employ a responder complex that is in any of the configurations set forth above. In some embodiments, the components of the responder and reactivator complex are linked covalently. Often, the plurality of responder complexes is a plurality of one responder complex that comprises a particular binding ensemble member. In other embodiments, the plurality of responder complexes may comprise complexes that are different, i.e., that comprise at least two different candidate binding ensemble members.

In another aspect, the invention provides a method of interaction mapping, comprising the steps of: providing a plurality of responder complexes comprising a plurality of candidate binding ensemble members; providing a plurality of reactivator complexes comprising a binding ensemble member linked to a reactivator molecule; combining the plurality of responder complexes with the plurality of reactivator complexes; and detecting an activity of the responder molecule, thereby detecting interaction between the binding ensemble member and at least one of the plurality of candidate binding ensemble members. The method may employ a responder complex that is in any of the configurations set forth above. In some embodiments, the components of the responder and reactivator complex are linked covalently. Often, the plurality of reactivator complexes is a plurality of a single reactivator complex that comprises a particular binding ensemble member. In other embodiments, the plurality of responder complexes may comprise complexes that are different, i.e., that comprise at least two different candidate binding ensemble members.

In another aspect, the invention provides a method for improving the affinity of a first binding pair member, the method comprising the steps of: providing a plurality of a first binding pair member; providing a plurality of a reactivator complex comprising a reactivator molecule and a second binding pair member; providing a plurality of responder complexes comprising a plurality of a responder molecule, a plurality of an inhibitor, and a plurality of candidate binding pair members, wherein the plurality of candidate binding pair members comprises variants of the first binding pair member; combining the reactivator complexes, the responder complexes, and the plurality of the first binding pair member, wherein a responder molecule is activated when a candidate binding pair member binds to a second binding pair member; and wherein the activity of the responder molecule is proportional to the affinity of the candidate binding pair members for the second binding pair member; and detecting an activity of the responder molecule corresponding to an affinity of the candidate binding pair member for the second binding pair member that is greater than that of the first binding pair member for the second binding pair member. The responder complex may be in any of the configurations described above. Often, the members of the responder and reactivator complexes are linked covalently.

The invention also provides a method for improving the affinity of a first binding pair member, the method comprising the steps of: providing a plurality of a first binding pair member; providing a plurality of a responder complex comprising a responder molecule, an inhibitor, and a second binding pair member; providing a plurality of reactivator complexes comprising a plurality of a reactivator molecule and a plurality of candidate binding pair members, wherein the plurality of candidate binding pair members comprise variants of the first binding pair member; combining the reactivator complexes, the responder complexes, and the plurality of the first binding pair member, wherein a responder molecule is activated when a candidate binding pair member binds to a second binding pair member; and wherein the activity of the responder molecule is proportional to the affinity of the candidate binding pair member for the second binding pair member; and detecting an activity of the responder molecule corresponding to an affinity of the candidate binding pair member for the second binding pair member that is greater than that of the first binding pair member for the second binding pair member. The responder complex may be in any of the configurations described above. Often, the members of the responder and reactivator complexes are linked covalently.

In addition, the invention provides a method for isotropic selection of a plurality of binding molecules, the method comprising the steps of: providing a plurality of responder complexes comprising a responder molecule, an inhibitor, and a first member of a binding ensemble; providing a first plurality of reactivator complexes comprising a plurality of candidate binding ensemble members, wherein each candidate binding ensemble member is individually linked to a reactivator molecule; combining the plurality of responder complexes with the plurality of reactivator complexes; detecting a first set of binding molecules, each of which binds to the first member of the binding ensemble, by detecting a responder activity when one of the candidate binding molecules bind to the first member of the binding ensemble; providing a plurality of responder complexes, each comprising a responder, an inhibitor, and a binding molecule from the first set of binding molecules; providing a second plurality of reactivator complexes comprising a plurality of candidate binding ensemble members, wherein each candidate binding ensemble member is individually linked to a reactivator molecule; providing a plurality of the first member of the binding ensemble; combining the plurality of responder complexes, the plurality of reactivator complexes, and the plurality of the first member of the binding ensemble; and detecting the responder activity when the binding molecule from the first set of binding molecules and a candidate binding molecule are bound simultaneously to the first member of the binding ensemble. In some embodiments, the first plurality of reactivator complexes and the second plurality of reactivator complexes are the same.

An additional method for isotropic selection of a plurality of binding molecules is also provided. The method comprises the steps of: providing a first plurality of responder complexes comprising a plurality of candidate binding ensemble members wherein each candidate binding ensemble member is individually mixed with a responder molecule, and an inhibitor; providing a plurality of reactivator complexes comprising a reactivator linked to a first member of a binding ensemble; combining the first plurality of responder complexes with the plurality of reactivator complexes; detecting a first set of binding molecules, each of which binds to the first member of the binding ensemble, by detecting a responder activity when the candidate binding molecules bind to the first member of the binding ensemble; providing a second plurality of responder complexes comprising a plurality of candidate binding ensemble members wherein each candidate binding ensemble member is individually mixed with a responder molecule, and an inhibitor; providing a plurality of reactivator complexes, each comprising a reactivator linked to a binding molecule from the first set of binding molecules; providing the plurality of the first member of the binding ensemble; combining the second plurality of responder complexes, the plurality of reactivator complexes, and the plurality of the first member of the binding ensemble; and detecting the responder activity when the binding molecule from the first set of binding molecules and a candidate binding molecule are bound simultaneously to the first member of the binding ensemble. Often, the first plurality of responder complexes and the second plurality of responder complexes are the same.

In another method of isotropic selection of a plurality of binding molecules, the steps comprise: providing a plurality of responder complexes comprising a plurality of candidate binding ensemble members wherein each candidate binding ensemble member is individually linked to the responder molecule and the inhibitor; providing a plurality of reactivator complexes comprising a plurality of candidate binding ensemble members, wherein each candidate binding ensemble member is individually linked to a reactivator molecule; providing a plurality of a first member of a binding ensemble; combining the plurality of responder complexes, the plurality of reactivator complexes and the plurality of the first member of the binding ensemble, wherein each combination is comprised of one responder complex, one reactivator complex, and the first binding ensemble member; and detecting a responder activity when a binding molecule from the first set of candidate binding molecules and a binding molecule from the second set of candidate binding molecules are bound simultaneously to the first member of the binding ensemble.

BRIEF DESCRIPTION OF THE DRAWINGS

FIG. 1 depicts two types of reactivator, inhibitor-binding and responder-binding. In A. the reactivator binds to the inhibitor with a higher affinity than that of the inhibitor for the responder, so that when the reactivator is docked to the responder-inhibitor complex by the subject molecule interaction, the binding equilibrium of the inhibitor is shifted from the responder to the reactivator, and the responder is thereby activated. In B. the reactivator binds to the responder with higher affinity than that of the inhibitor for the responder, and without inhibiting it, so that when docked by the subject molecule interaction the reactivator displaces the inhibitor from the responder, and the latter is activated.

DETAILED DESCRIPTION OF THE INVENTION

Definitions

Figure 1:
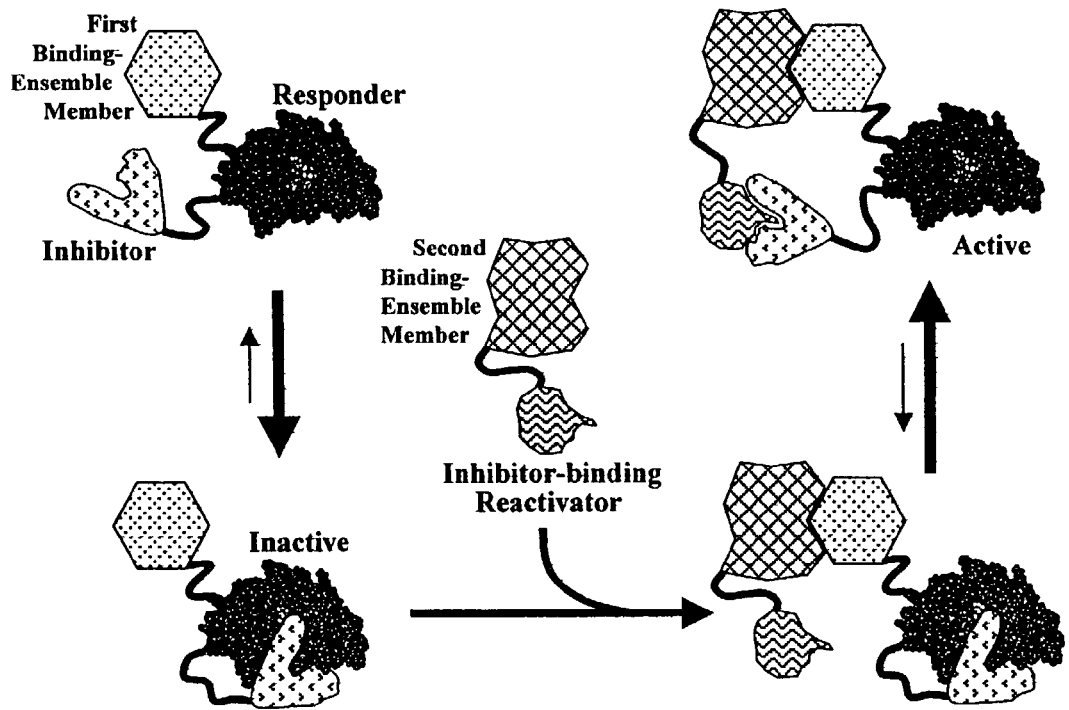
FIG. 1 illustrates interaction-mediated reactivation of a cis-inhibited responder. In this embodiment, the responder is in a tri-partite fusion with a binding ensemble member and an inhibitor of the responder, such that the enzyme is constitutively inactive. No particular order of elements is preferred. A second binding ensemble member is fused to a reactivator.
Figure 1:
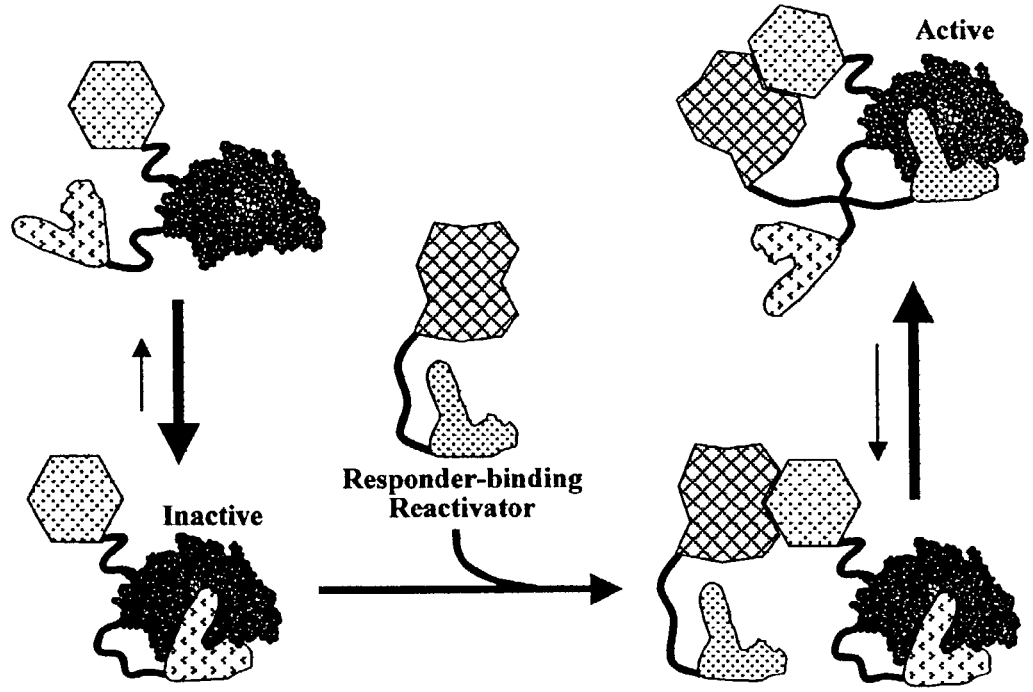

The terms "affinity matured" in the context of binding ensemble members refers to a member that is derived from a reference binding ensemble member by, e.g., mutation, insertion, and/or deletion, binds to the same binding ensemble member as the initial reference member, and has a higher affinity for that binding ensemble member than that of the reference binding member. In a preferred embodiment, the affinity matured member binds to the same site as the initial reference member.

"Antibody" refers to a polypeptide comprising at least a heavy chain variable region and a light chain variable region that together specifically bind and recognize an antigen, the variable regions being specified by immunoglobulin genes. Recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chain variable regions respectively.

As used herein "antibody" may also refer to any functional, i.e., capable of binding specifically to an epitope, VH and VL pair that are each linked in various configurations to other polypeptide(s) that may perform various functions, e.g., as responder, inhibitor, or stabilizer of the VH-VL complex.

Antibodies exist, e.g., as intact immunoglobulins, as a number of well-characterized fragments produced by digestion with various peptidases, or as well-characterized fragments produced by recombinant gene expression. Thus, for example, pepsin digests an antibody below the disulfide linkages in the hinge region to produce F(ab)'2, a dimer of Fab which itself is a light chain joined to VH-CH1 (Fd fragment) by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)).

"Binding" refers to the non-covalent adherence of molecules to one another, for example, enzymes to substrates, antibodies to antigens, DNA strands to their complementary strands. Binding occurs because the shape and chemical natures of parts of the molecules surfaces are complementary.

"Binding affinity" is generally expressed in terms of equilibrium association or dissociation constants ($K_a$ or $K_d$, respectively), which are in turn reciprocal ratios of dissociation and association rate constants ($k_d$ and $k_a$, respectively). Thus, equivalent affinities may comprise different rate constants, so long as the ratio of the rate constants remains the same.

A "binding ensemble member" refers to a molecule that participates in a specific binding interaction with another member of the binding ensemble. A binding ensemble often comprises two members, i.e., a binding pair, but can comprise three or more members. For example, an antigen and two antibodies that recognize two different epitopes on the antigen and can be bound to the antigen at the same time comprise a binding ensemble. The "third" member, e.g., an antigen, brings the first and second members of the binding ensemble, e.g., two antibodies, into proximity. A third member of a binding ensemble need not be a single molecule, e.g., a single protein or polypeptide, but may comprise multiple subunits. The other members of the binding ensemble may therefore bind to either the same subunit or different subunits. For example, a cell and two antibodies that bind to two different epitopes on one cell surface protein or to two different cell surface proteins at the same time comprise a binding ensemble in which a "third" member, i.e., the cell, comprises multiple subunits.

Binding ensemble members can include antibodies/antigens, receptors/ligands, biotin/avidin, and interacting protein domains such as leucine zippers and the like, as well as components of supra-molecular structures such as ribosomes, transcription complexes, cytoskeletal structures, signal transduction complexes, and metabolic complexes. A binding ensemble member as used herein can be a binding domain, i.e., a subsequence of a protein that binds specifically to another member of the binding ensemble. In reference to binding pairs, the binding pair members can also be referred to as a binding pair member and a binding partner (or cognate binding partner). Binding ensembles can also include docking agents, i.e., members that are added to dock binding ensemble members to the responder and/or the inhibitor, or to the reactivator, such as, for example, biotin/avidin, antibody/antigen, or leucine zipper.

A "complex" as used herein refers to an assemblage of components that are linked, either covalently or non-covalently, e.g., via a binding interaction. As appreciated by one of skill in the art, components that are linked by a binding interaction will typically be in an equilibrium, depending on the affinity and concentration of the components.

"Docking" and "dock" refer to a binding interaction between two molecules which brings other molecules into proximity, which other molecules are linked to the docking molecules.

"Domain" refers to a unit of a protein or protein complex, comprising a polypeptide subsequence, a complete polypeptide sequence, or a plurality of polypeptide sequences where that unit has a defined function. The function is understood to be broadly defined and can be binding to a binding partner, catalytic activity, structural activity, or can have a stabilizing effect on the structure of the protein. "Domain" also refers to a structural unit of a protein or protein complex, comprising one or more polypeptide sequences where that unit has a defined structure which is recognizable within the larger structure of the native protein. The domain structure is understood to be semi-autonomous in that it may be capable of forming autonomously and remaining stable outside the context of the native protein.

The term "expression vector" includes vectors which are capable of expressing nucleic acid sequences contained therein, i.e., any nucleic acid sequence which is capable of effecting expression of a specified nucleic acid code disposed therein (the coding sequences are operably linked to other sequences capable of effecting their expression). Some expression vectors are replicable in the host organism either as episomes or as an integral part of the chromosomal DNA. A useful, but not a necessary, element of an effective expression vector is a marker encoding sequence—i.e. a sequence encoding a protein which results in a phenotypic property (e.g. tetracycline resistance) of the cells containing the protein which permits those cells to be readily identified. Expression vectors are frequently in the form of plasmids or viruses. However, the invention is intended to include such other forms of expression vectors which serve equivalent functions and which may, from time to time become known in the art.

"Heterologous", when used with reference to portions of a protein, indicates that the protein comprises two or more domains that are not found in the same relationship to each other in nature. Such a protein, e.g., a fusion protein or a conjugate protein, contains two or more domains from unrelated proteins arranged to make a new functional protein. Heterologous may also refer to a natural protein when it is found or expressed in an unnatural location such as when a mammalian protein is expressed in a bacterial cell.

As used herein "immunoglobulin variable region domain" refers to any VH or VL domain used as a binding moiety without a companion VH or VL domain. As with antibodies, such domains may be linked in various configurations to other polypeptide(s) that may perform various functions, e.g., as responder, inhibitor, or reactivator.

An "inhibitor" refers to a molecule that can inhibit the responder when both are in the responder complex. In one embodiment, the inhibitor, a binding ensemble member, and the responder are linked together. In an alternative embodiment, the inhibitor is linked to a binding ensemble member and the responder is free in solution.

A "low-affinity inhibitor" is a relative term referring to an embodiment of the inhibitor where the inhibitor has a $K_d$ (equilibrium dissociation constant) for the responder which is at least ten-fold higher than the working concentration of the inhibitor, such that the inhibitor cannot bind to the responder to an appreciable extent without a heterologous mechanism for bringing the two together.

As used herein "interaction" refers generally to attractive physical interactions, i.e., the binding of two or more molecules into a supra-molecular complex which is stable in the sense that each component has an affinity for at least one other member of the complex corresponding to a $K_d$ of $\leq 1$ mM.

The term "interaction" or "interacts" when referring to the interaction of binding ensemble members generally refers to binding to one another. However, it may also refer to indirect interaction mediated by other molecules, usually additional binding ensemble members. Accordingly, a molecule that interferes with the binding interaction of binding ensemble members with one another decreases or prevents binding of a binding ensemble member to another member of the binding ensemble. Typical binding pairs include antibodies/antigens, receptor/ligands, subunits of multimeric proteins or supra-molecular structures. "Binding" or "interacting" as used herein refers to noncovalent associations, e.g., hydrogen bonding, ionic bonding, electrostatic bonding, hydrophobic interaction, Van der Waals associations, and the like.

The term "library of expressed sequences" refers to any population of nucleotide sequences which are derived from messenger RNA, and which are therefore understood to encode polypeptide sequences, or fragments thereof, that are produced naturally in cells.

As used herein "ligand" refers to a molecule that is recognized by, i.e., binds to, a particular receptor. As one of skill in the art will recognize, a molecule (or macromolecular complex) can be both a receptor and a ligand, typically when both are soluble or both are membrane-bound. However, when one is membrane-bound and the other is soluble, the former is commonly referred to as the receptor and the latter is the ligand. When both are soluble, the binding partner having a smaller molecular weight is typically referred to as the ligand and the binding partner having a greater molecular weight is referred to as a receptor. More generally, the binding partners of non-receptor proteins may also be referred to as ligands.

A "linker" or "spacer" refers to a molecule or group of molecules that covalently connects two molecules, such as a binding pair member and a responder or an inhibitor, and serves to place the two molecules in a preferred configuration, e.g., so that a responder can interact with an activator or inhibitor with minimal steric hindrance from a binding pair member, and a binding pair member can bind to a binding partner with minimal steric hindrance from the responder or inhibitor. A "flexible linker" refers to a peptide linker of any length in which the amino acid composition minimizes the formation of rigid structure by interaction of amino acid side chains with each other or with the polypeptide backbone. Typically a "flexible linker" is rich in glycine. An example of such a linker has the composition $(Gly_4Ser)_x$, where "x" may typically vary from 1 to 10.

"Link" or "join" or "fuse" refers to any method of functionally connecting peptides, typically covalently, including, without limitation, recombinant fusion of the coding sequences, and covalent bonding (e.g., disulfide bonding). In the systems of the invention, a binding pair member is typically linked or joined or fused, often using recombinant techniques, at the amino-terminus or carboxyl-terminus by a peptide bond to a responder or to an activator or inhibitor of the responder. However, the binding pair member may also be inserted into the responder or inhibitor at an internal location that can accept such insertions. The binding pair member can either directly adjoin the fragment to which it is linked or fused or it can be indirectly linked or fused, e.g., via a linker sequence. "Linked" may also refer to a non-covalent physical association, particularly one which is constitutive, i.e., does not require docking, under operating conditions. For example, in a responder mixture comprised of responder, inhibitor, and binding ensemble member, each component is typically linked to at least one other component, either covalently, e.g., via peptide linkage, or non-covalently, via high-affinity binding interaction.

A "member" or "component" in the context of a responder system refers to a responder, a fragment or subsequence of a responder, a subunit of a responder, or an activator or inhibitor of the responder. The responder can be a complete polypeptide, or a fragment or subsequence thereof that retains responder activity.

The term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A "reactivator" as used herein refers to a molecule, typically a protein, that can displace an inhibitor from a responder and thereby activate the responder. In one embodiment, the reactivator binds to the inhibitor. In an alternative embodiment, the reactivator binds to the responder. In another embodiment, the reactivator binds anywhere on the responder complex, e.g., at a junction between two components of the responder complex or to two components of the complex. In preferred embodiments, the binding of reactivator occurs only when it is brought into proximity with the inhibited responder by interaction of the binding ensemble members of the reactivator and responder complexes.

The term "reactivator complex" refers to a complex comprised of the reactivator and a binding ensemble member. The reactivator and the binding ensemble member may be complexed together by a binding interaction. In another embodiment, the reactivator and binding ensemble member are part of the same polypeptide chain. In a preferred embodiment, the reactivator complex include a linker.

"Recombinant nucleic acid" refers to a nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

"Recombinant polypeptide" refers to a polypeptide expressed from a recombinant nucleic acid, or a polypeptide that is chemically synthesized in vitro.

A "reference binding ensemble member" is a known binding ensemble member for which the practitioner wants to obtain a variant with higher binding affinity, i.e., an "improved" binding pair member.

The term "responder" refers to any protein that produces a detectable signal, including, but not limited to detectable signals such as fluorescence, enzymatic activity, a selectable phenotype (e.g., antibiotic resistance), a screenable phenotype, or that produces an activity that results in a phenotypic change or provides a functional product that is detectable.

The term "reporter" as used herein, refers to a responder that produces a detectable signal, or that confers a selectable phenotype.

The term "responder complex" refers to a complex comprised of the responder, the inhibitor, and a binding ensemble member. One or more members of the responder complex may be complexed with the others by a binding interaction. At least one member of the responder complex may also be in the same polypeptide chain as at least one other member. In a preferred embodiment, all three members of the responder complex are in the same polypeptide chain.

As used herein, the term "single-chain antibody" (scFv) refers to a polypeptide comprising a $V_H$ domain and a $V_L$ domain in polypeptide linkage, generally linked via a spacer peptide (e.g., [Gly-Gly-Gly-Gly-Ser]$_x$), and which may comprise additional amino acid sequences at the amino- and/or carboxyl-termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino acids substantially encoded by genes of the immunoglobulin superfamily (e.g., see The Immunoglobulin Gene Superfamily, A. F. Williams and A. N. Barclay, in Immunoglobulin Genes, T. Honjo, F. W. Alt, and T. H. Rabbitts, eds., (1989) Academic Press: San Diego, Calif., pp.361-387, which is incorporated herein by reference), most frequently encoded by a rodent, non-human primate, avian, porcine, bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The term "target molecule" is used to refer to a binding ensemble member which is being tested for its presence in a sample or specimen, e.g., a clinical, biological, or environmental sample, or which is being used as a "homing" device to co-locate cis-inhibited responder and reactivator at a specific location, e.g., at the site of a tumor in the body, or which is being used as a switch (wherein it may also be called a "switch molecule") to activate a responder, e.g., at a desired time. In one embodiment, a "target molecule" binds to two members of a binding ensemble, one of which is linked to the cis-inhibited responder and the other of which is linked to the reactivator, such that the responder and reactivator are brought into mutual proximity, and the former is reactivated thereby. The target molecule can be any of a number of molecules including peptides, chemicals, carbohydrates, lipids, etc.

A "scaffolded peptide" refers to a peptide, typically of up to about 20 amino acids in length, that is inserted into a natural protein at a location known to accept such insertions without interfering with the folding or native configuration of the protein (A Skerra, *J Mol Recognit* 13:167-87, 2000). Usually the location is on the surface of the protein. Often, the peptide is not a known natural sequence, and therefore is not expected to fold into a stable structure on its own, but generally assumes a random coil structure in solution. However, when inserted into the scaffold protein the peptide is expected to acquire some degree of stable structure by packing against the surface of the protein. Such structure generally improves the ability of the peptide to bind with high affinity to other molecules, such as other proteins. Many proteins may serve as scaffolds for random peptide libraries. Frequently, surface loops between elements of secondary structure such as α-helices or strands of a β-sheet may accept such insertions without significant perturbation of folding or structure. Examples of proteins that have been used as scaffolds include, but are not limited to, thioredoxin (or other thioredoxin-like proteins), nucleases (e.g., RNase A), proteases (e.g., trypsin), protease inhibitors (e.g., bovine pancreatic trypsin inhibitor), antibodies or structurally-rigid fragments thereof, and other domains of the immunoglobulin superfamily.

Each of the above terms is meant to encompass all that is described, unless the context dictates otherwise.

Introduction

The detection systems disclosed herein overcome many limitations of molecular detection systems in the art, such as component instability and weak activity, and allow applications that are not possible or practical with prior art systems, e.g., therapeutic applications or in vitro applications. This invention provides novel methods and systems for linking the activity of a responder protein to the interaction of two or more binding ensemble members of interest, either in vitro or in vivo, and thereby producing a signal, phenotype, or other functional output in response to the interaction of the binding ensemble members.

The systems of the invention comprise the following components: a responder protein, an inhibitor of the responder, an inhibitor of the inhibitor, i.e., a "reactivator" of the responder protein, and interacting components that comprise the binding ensemble members. The system basically operates such that, in the absence of a binding interaction between binding ensemble members, the inhibitor inhibits the activity of the responder molecule. When a binding interaction occurs between two or more binding ensemble members, the reactivator displaces the inhibitor from the responder molecule. Detection of responder molecule activity, or of a desired level of responder molecule activity, thus indicates the presence of a binding interaction.

Figure 3:
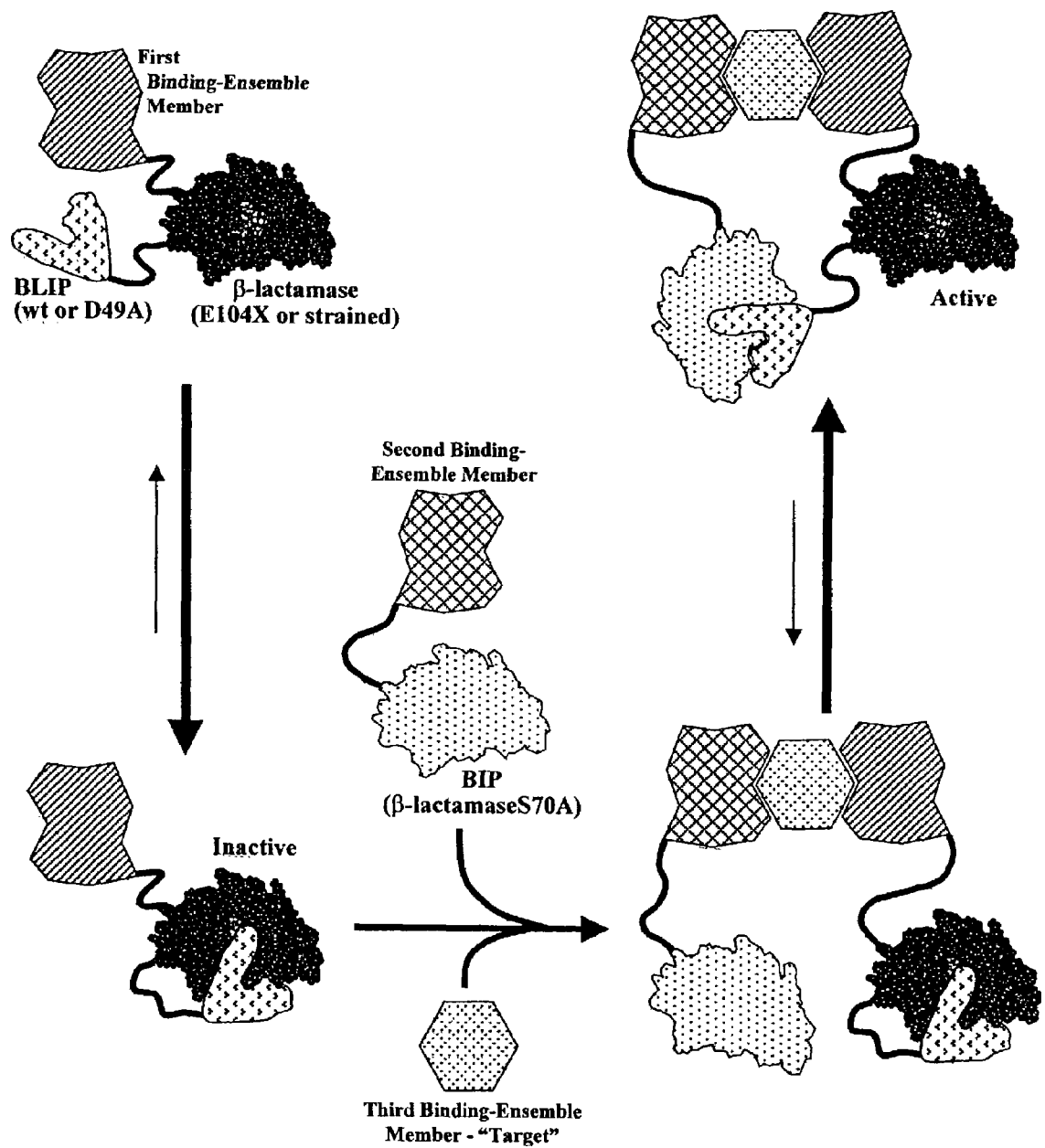
FIG. 3 illustrates target-mediated reactivation of BLIP-inhibited β-lactamase. In this embodiment, a third binding ensemble member, the target, to which the first two members are bound simultaneously, is required to facilitate the docking of the reactivator, in this case BIP, to the BLIP-β-lactamase complex.

The system components can be arranged in a number of different configurations. In one embodiment, a first member of a binding ensemble is linked via a flexible linker to a fusion of the responder molecule and an inhibitor of the responder; and a second binding ensemble member is linked to the reactivator molecule (see, e.g., FIG. 1). Alternatively, the first member of the binding ensemble may be linked to a high-affinity inhibitor of the responder molecule with the responder being unlinked (see, e.g., FIG. 4); or the binding ensemble member may be linked to the responder with the inhibitor being unlinked. In another embodiment, the reactivator and the second binding ensemble member are complexed by a binding interaction rather than a covalent linkage. In all of these embodiments, the responder protein is constitutively bound by the inhibitor, and is therefore inactive, when the binding ensemble members do not interact. When the first and the second binding ensemble members interact, either directly, or via one or more additional subject molecules (see, e.g., FIG. 3), the inhibitor is displaced from the responder by the reactivator, so that the responder becomes functionally active. Displacement of the inhibitor by the reactivator may be direct (e.g., competitively) or indirect (e.g., allosterically).

In a preferred embodiment, the responder and inhibitor of the responder are fused to one another via a flexible linker, such that the responder is constitutively inhibited in cis (i.e., on the same conjugate molecule), or "masked". This masked responder and the reactivator are each fused, via flexible linkers, to different binding ensemble members, such that interaction of the binding ensemble members, either directly or via one or more additional binding ensemble members, facilitates displacement of the inhibitor from the responder by the reactivator, thereby causing functional reactivation of the responder (see, e.g., FIG. 1). The components of the system may be deployed in vitro, as in an assay for an analyte in a biological specimen, or they may be expressed in cells, as in a selection system for protein-protein interactions or antibodies for a particular antigen.

Current homogeneous enzymatic assays rely on inhibition of the enzyme by binding of anti-analyte antibody to the analyte, or mimic thereof, immobilized on the surface of the enzyme (Coty et al., (1994) *J Clin Immunoassay* 17: 144-150). Free analyte is estimated by its ability to competitively displace the antibody, thereby activating the enzyme. For assays employing such enzymes the maximum signal increment occurs at equilibrium with roughly $K_d$ concentrations of reagents, so that typically only a fraction of analyte molecules participates in signal generation, and equilibration is often slow or does not even reach completion. However, an enzyme responder, which is activated by direct allosteric interaction with analyte, can be used in excess, so that equilibration is rapid and independent of the analyte concentration, and the analyte can be saturated to produce signal from every molecule. In the case of microbial or viral pathogens, where unique surface markers may be present in hundreds to thousands of copies per cell or particle, such enzymes, which would be activated by binding to the marker, can allow rapid detection of as little as a single cell or particle, whereas the sensitivity of equilibrium assays for such analytes would typically be much lower.

The systems disclosed herein offer significant advantages for use as biosensors. Biosensors are devices for automated electronic or optical detection and quantification of analytes (Lowe (1989) *Philos Trans R Soc LondB Biol Sci.*, 324:487-96). They are extremely useful in many different types of automated process control, from pharmaceutical and industrial purification processes to the monitoring of toxic substances in natural resources and the environment. Most current biosensor platforms are quite limited in the types of molecules they can detect. For example, most require enzymatic oxidation or other chemical transformation of the analyte. A few biosensors work by coupling specific analyte binding to the enzymatic generation of an electrical or optical signal, but these are generally limited to a small number of applications. Systems of the present invention can be set up to couple the binding of any analyte, including small molecules, macromolecules, viruses, and cells, to the generation of electrical or optical signals by using an appropriate enzyme or fluorescent responder protein with an inhibitor and a reactivator linked to binding ensemble members that can be coupled by binding to the analyte (which is also a binding ensemble member), whereupon the responder is activated and an electrical or optical signal is generated which is directly proportional to the absolute amount of analyte in the sample.

Systems of the present invention can also be used to activate effector molecules upon binding to specific cell surface molecules. This would allow the effector to become localized and activated at specific sites in the body for target-restricted activation of reagents for therapy or imaging. Antibody-Directed Enzyme Prodrug Therapy (ADEPT; Bagshawe (1995) *Drug Devel Res* 34: 220-30) is a promising chemotherapeutic strategy for the treatment of cancer, in which a prodrug-activating enzyme, such as a β-lactamase, is targeted to the tumor by a tumor-specific antibody to which it is chemically or genetically conjugated. After unbound conjugate has cleared the circulation, an inactive prodrug, such as an anthracycline cephalosporin, is administered, which is converted to a potent tumor-killing cytotoxin at the site of the tumor by the remaining tumor-bound enzyme. The main problem with ADEPT is that the unbound conjugate must clear the circulation before the prodrug can be administered in order to minimize systemic toxicity. However, by the time the conjugate has cleared the circulation >90% of the tumor bound enzyme has been lost (Bagshawe (1995) *Drug Devel Res* 34: 220-30; Springer and Niculescu-Duvaz (1995) *Anti-Cancer Drug Design* 10: 361-72). In spite of this, ADEPT has been able to achieve higher active drug concentrations in the tumor than any other procedure (Sedlacek et al. in *Contributions to Oncology*, Huber and Queisser, eds., Karger, Basel (1992) pp. 208ff), and has shown promise in the clinic (Bagshawe et al., (1991) *Disease Markers* 9: 233-238; Springer and Niculescu-Duvaz (1995) *Anti-Cancer Drug Design* 10: 361-72; Martin et al. (1997) *Cancer Chemother Pharmacol* 40: 189-201). The unbound conjugate problem could be completely obviated by a prodrug-activating enzyme which would be active only when bound to the tumor, so that the prodrug could be administered simultaneously with the enzyme or at the point of peak tumor loading without regard for unbound enzyme which would be inactive.

In the same way, systems of the present invention can be targeted for activation by surface markers on other types of cells and tissues, such as pathogen-infected cells, transplants, and sites of inflammation or atherogenesis. The target-localized and activated enzymes can then be used to activate not just cytotoxins, but other types of therapeutic agents such as small molecule agonists or antagonists of biological response modifiers, as well as imaging reagents for precise localization of tissue with disease or other phenotype of interest. For example, target-activated enzymes may be used to deliver: (1) immune stimulants to tumors, (2) immuno-suppressants to sites of chronic inflammation or to organ transplants to inhibit rejection, (3) antibiotics to specific pathogens, (4) cytotoxins and anti-virals to virus-infected cells, (5) hormones and other pleiotropic agents to specific cells and/or tissues, or (6) neuro-transmitters and other neuro-modulators to specific nerves or tissues. In short, target-activated enzymes may be used to deliver to any tissue any small molecule cytotoxin, hormone, steroid, prostaglandin, neurotransmitter, or agonist/antagonist of peptide hormone, cytokine, or chemokine, etc., which can be inactivated by conjugation to the appropriate substrate.

Target-activated enzymes of the present invention can be used in vivo as sensors for rapid detection of the activation or inhibition of key steps in metabolic, signal transduction, cell cycle regulation, or gene expression pathways, enabling high-throughput cellular screens for inhibitors or activators of those pathways. For example, screening for agonists or antagonists of receptor tyrosine kinases or G-protein-coupled receptors usually requires coupling receptor ligation to a selectable phenotype which results from de novo gene expression. Such multi-step signal generating mechanisms are prone to high rates of false positive and false negative selection, severely compromising their efficiency for high-throughput screening. However, target-activated enzymes of the present invention may be set up for activation by phospho-tyrosine-containing or GTP-bound signal transducers, so that a selectable phenotype is generated just downstream from receptor ligation. Interaction between the signal transducer and the enzyme may be designed to be either dependent on, or inhibited by phosphorylation or bound GTP/GDP, so that either receptor agonists or receptor antagonists can be selected.

Responders

Responders include any protein that produces a detectable signal, a selectable phenotype, or which performs a useful function in response to the interaction of binding ensemble members. For example, enzymes such as β-lactamase may be used to generate a color signal from chromogenic or fluorogenic substrates, or to confer an antibiotic resistance phenotype on host bacterial cells, or to activate a cephalosporin prodrug to produce a cancer-killing drug upon interaction with, i.e., binding to a cancer marker. Other enzymes that can be used as responder proteins include those that hydrolyze chromogenic or fluorogenic substrates to yield a colored or fluorescent product. These include, for example, β-galactosidase, alkaline phosphatase, peroxidases, esterases, carboxypeptidases, glycosidases, glucuronidases, and carbamoylases. Still other useful enzymes are listed in U.S. Pat. No. 6,220,964 (which is incorporated by reference), and include penicillin-amidases, aminoglycoside phosphotransferases, e.g., neomycin phosphotransferase, puromycin N-acetyltransferase (Sanchez-Puig et al., *Gene* 257:57-65, 2000, incorporated by reference), and chloramphenicol acetyl transferase.

Non-enzymatic molecules can also be employed as responders using the methods of the invention. For example, biological response modifiers, such as insulin, can be used to activate useful cellular functions, such as glucose uptake in insulin-dependent diabetics, in response to the presence of subject molecules, such as glucose. Fluorescent proteins such as the green fluorescent protein (GFP) of *Aequorea Victoria* (Chalfie et al., (1994) *Science* 263: 802-805) can also be employed as responders. GFP absorbs blue light and fluoresces green. GFP fluorescence can be quenched or shifted in cis by fusing it to a protein or other molecule that perturbs the chromophore. Reactivators can be fashioned from proteins or other molecules that bind to the quencher/shifters, thereby preventing them from binding to GFP. With such components GFP can be used in systems of the present invention.

Further examples of responder molecules can be found in U.S. Pat. Nos. 6,294,330; 6,220,964; 6,342,345; and/or U.S. patent application Ser. No. 09/526,106, filed on Mar. 15, 2000, which are hereby incorporated by reference.

Inhibitors

Figure 2:
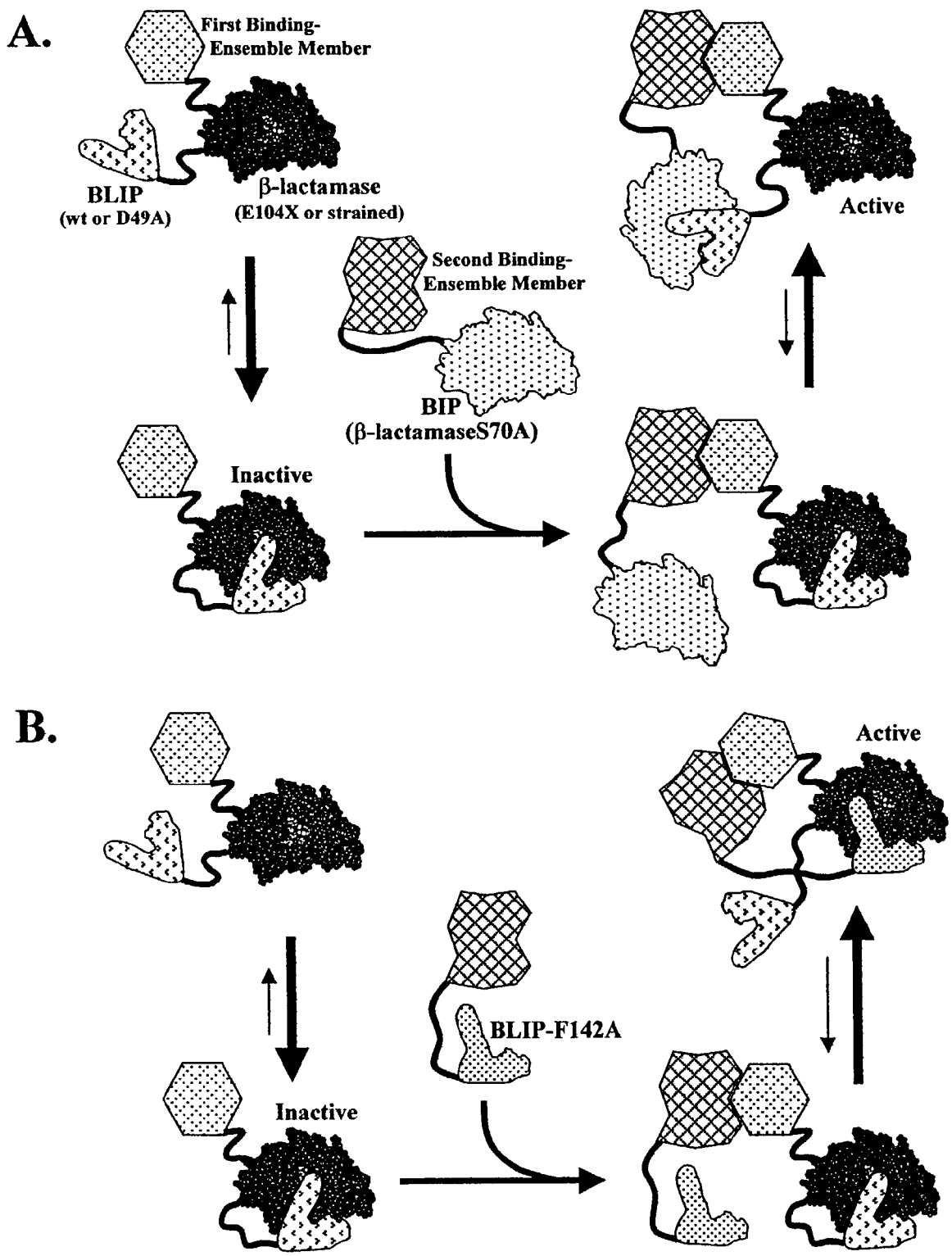
FIG. 2 illustrates interaction-mediated reactivation of BLIP-inhibited β-lactamase by an inhibitor binding reactivator, BIP (A.), and by a responder binding reactivator, BLIP-F142A (B.). BLIP-F142A competes with BLIP for binding to β-lactamase, but does not inhibit the enzyme. The affinity between inhibitor BLIP and β-lactamase is reduced by linker-induced strain and/or by using reduced-affinity mutations such as E104K, Q, D, or A in β-lactamase, or D49A in BLIP. This allows quantitative displacement of the inhibitor by the reactivator when the latter is docked to the BLIP-β-lactamase complex by an interaction of binding ensemble members which are linked to the the BLIP-β-lactamase complex and to the BLIP-F142A reactivator, respectively. The β-lactamase structure is a space-fill model rendered from the x-ray coordinates of Jelsch et al., 1993 (Proteins Struct. Funct. 16, 364ff) using the WebLab ViewerPro 3.7 program (Molecular Simulations, Inc.).

Inhibitors may include natural inhibitors or artificial inhibitors. In the present invention inhibitors include polypeptides, nucleic acids, carbohydrates, other macromolecules, or small molecules (i.e., <1 kDa MW). Many responders have known natural inhibitors which may be used in the invention. For example, the β-lactamase Inhibitor Protein (BLIP; Strynadka et al, (1994) *Nature* 368: 657-660) is a 165 amino acid natural inhibitor of β-lactamase which may be used in the present invention when β-lactamase is the responder (see, e.g., FIG. 2). Many proteases also have natural protein inhibitors, e.g., thrombin and anti-thrombin, trypsin has many inhibitors, etc. (Beynon and Bond, *Proteolytic Enzymes, a Practical Approach*, IRL Press, Oxford, UK, 1989). Other inhibitors known in the art include: pyridindolol for beta-galactosidase; urethane for firefly luciferase; the bacterial luciferase inhibitor reported in Kratasiuk et al., (1978) *Biokhimiia* 43(8):1369-76; Src kinase specific inhibitor PP2; and Rho-kinase specific inhibitor Y-27632.

Inhibitors may be selected from any of the small molecule/combinatorial libraries that are well-known in the art (see e.g., U.S. Pat. Nos. 6,294,330, 6,343,257, 6,281,245, 6,274,716, 6,255,120, 6,239,152, 6,207,820, 6,191,256, 6,127,191, 6,093,798, 5,977,328, 5,965,718, 5,962,337, 5,958,792, 5,877,278, 5,792,821, 5,766,963, 5,663,046, 5,549,974, hereby incorporated by reference).

Inhibitors may also be selected from random peptide libraries or from natural populations of binding proteins with diverse binding specificities such as antibodies or immunoglobulin variable region domains. Random peptide libraries may be incorporated into the sequence of a suitable scaffold protein such that upon folding of the scaffold protein the peptides are displayed or "scaffolded" on the protein surface (see, e.g., Skerra (2000) *J Mol Recognit.* 13:167-87). Many different proteins may be used as scaffolds. These proteins are typically small in size (e.g., less about 200 amino acids), rigid in structure, of known three dimensional configuration, and are able to accommodate insertions of peptides of interest into exposed loops without undue disruption of their structures. They are capable of stable expression in both prokaryotic and eukaryotic hosts. Typically such scaffold proteins can be stably expressed at high levels in various prokaryotic and eukaryotic hosts, or in suitable cell-free systems. Furthermore, the scaffold proteins are generally soluble and resistant to protease degradation. For example, thioredoxin has been widely used. Peptide libraries, typically of 6-20 random amino acids, can be inserted into the active site of thioredoxin without disturbing its stability. Thioredoxin has the further advantage that it is much smaller than most natural inhibitors, and is therefore less sterically constrained when access to the responder is restricted by linker lengths and the orientations of interacting subject molecules. Another good scaffold is the immunoglobulin domain, of which the antibody variable region domain is a prime example (Skerra (2000) *J Mol Recognit* 13:167-87). The immunoglobulin superfamily is one of the largest families of structurally homologous protein folds found in nature (Hawke et al. (1999) *Immunogenetics* 50:124-33). Immunoglobulin domains are comparable in size to thioredoxin and tolerate random peptide libraries in a number of exposed loops in the structure. Other scaffold proteins useful in the invention include RNase A, proteases (e.g., trypsin), and protease inhibitors (e.g., bovine pancreatic trypsin inhibitor).

Any of a variety of systems that detect protein-protein interactions, such as bacteriophage display (*Phage Display of Peptides and Proteins* Kay, Winter, and McCafferty, Eds. (1997) Academic Press, San Diego) or β-lactamase fragment complementation (U.S. patent application Ser. No. 09/526,106) or the system of the invention (using a responder with an already defined inhibitor and reactivator) can be used to select inhibitors that can be used in the present invention. For example, a thioredoxin-scaffolded peptide (trxpep) library can be displayed on the surface of filamentous bacteriophage, and panned against the immobilized responder molecule. Phage which bind to the responder can then be recovered, and the encoded trxpeps can be individually screened for their ability to inhibit the responder only when both are fused to interacting subject molecules. It is reasonable to expect that a substantial proportion of responder—binding trxpeps will also inhibit the function of the responder. In many cases, the responder itself may be used to screen trxpep libraries for inhibitors. The only requirement is that a null responder phenotype be selectable. For example, the responder and trxpep library can be fused to each member of a model binding pair, such as the leucine zipper helices from the c-fos and c-jun subunits of the AP-1 transcription factor, and expressed in cells. If the responder is fluorescent, or produces a colored or fluorescent product, an inhibitor trxpep will, upon docking to the responder by the binding pair interaction, render the host cells colorless or non-fluorescent, and this can be detected by eye or by flow cytometry.

For use with GFP in systems of the present invention, an inhibitor mask that quenches or shifts GFP fluorescence in cis can be selected from a random peptide library fused to either end of GFP via a flexible linker. A selectable phenotype-conferring responder, such as chloramphenicol acetyltransferase (CAT) or neomycin phosphotransferase (NPT II), can be fused via linker to the carboxyl terminus of the GFP/peptide library to ensure that selected masks do not quench by destabilizing GFP, in which case the selectable phenotype would also be quenched (see, e.g., co-pending U.S. patent application Ser. No. 09/510,097). The GFP/peptide-responder library is expressed in bacterial cells and plated on solid medium containing the selecting antibiotic (e.g., chloramphenicol or kanamycin) so that only cells that express stable GFP/peptide-responder fusions which confer antibiotic resistance can grow into colonies. Peptide inhibitors for GFP that are useful in the present invention are then identified by screening the colonies that exhibit no or weak fluorescence at the GFP emission maximum, when illuminated at the excitation maximum of wild-type GFP. GFP quenchers for use in the present invention can also be isolated from antibody, immunoglobulin variable region, or scaffolded peptide libraries by phage display methods (*Phage Display of Peptides and Proteins* Kay, Winter, and McCafferty, Eds. (1997) Academic Press, San Diego), or by using β-lactamase fragment complementation systems (U.S. patent application Ser. No. 09/526,106), or the systems of the invention.

Reactivators

Reactivators are molecules that can displace an inhibitor from a responder directly or indirectly. In one embodiment, the affinity of the reactivator for either the inhibitor or the responder is greater than the affinity of the inhibitor for the responder, so that the inhibitor is sterically excluded from binding with the responder (see, e.g., FIG. 1). Like inhibitors, reactivators may be selected from libraries of random peptides, scaffolded random peptides, antibodies, or other natural binding proteins. Reactivators may also be engineered from responders by introducing mutations which disable responder activity without imparing inhibitor binding or the stability of the reactivator. For example, a reactivator for β-lactamase may be engineered by mutating the active site serine (Ser) of the enzyme to alanine (Ala). This mutation renders β-lactamase catalytically inactive, but still fully capable of binding its natural inhibitor, BLIP. Because of the concentration effect, this BLIP Inhibitor Protein (BIP) is not able to activate β-lactamase at working concentrations when the latter is fused to BLIP. However, when docked to the β-lactamase BLIP complex by an interaction of subject molecules, BIP acts as a reactivator, i.e., it displaces BLIP from β-lactamase, thereby activating the latter (see, e.g., FIG. 2A). When the α-lactamase-BLIP affinity is reduced by, e.g., a D49A mutation in BLIP, and/or by an E104K, D, Q, or A mutation in β-lactamase, and/or by linker-induced strain, reactivation by BIP is favored, and may go to near completion.

Reactivators may also be engineered from inhibitors of responders by introducing mutations which impair inhibition of the responder active site without interfering with reactivator binding to the responder. For example, a reactivator for β-lactamase may be engineered by mutating phenylalanine (F) 142 of BLIP to alanine (A). This mutation impairs BLIP's ability to block the β-lactamase active site without impairing its ability to bind to β-lactamase (Petrosino et al., (1999) *J Biol Chem* 274:2394-2400). As with BIP, BLIP-F142A is not able to activate β-lactamase at working concentrations when fused to BLIP. However, when docked to the β-lactamase-BLIP complex by an interaction of subject molecules, BLIP-F142A is displaces BLIP from β-lactamase, thereby activating the latter (see, e.g., FIG. 2B). As with BIP, if the affinity of the β-lactamase-BLIP complex is reduced by strain from, e.g., a short linker, replacement of BLIP by BLIP-F142A will be favored, and may even go to near completion.

Reactivators can be selected from libraries of random peptides, scaffolded peptides, antibodies, or other binding molecules by fusing the library to a binding ensemble members, and co-expressing this library in appropriate cells under selective conditions with the appropriate responder complex. Cells exhibiting the screenable/selectable phenotype conferred by the activated responder protein, i.e., the activated responder protein, should be expressing reactivator molecules. Thus-selected reactivators must then be screened for docking dependence by testing for loss of the selectable phenotype when one of the binding ensemble members is substituted with a non-ensemble member. For example, a random hexameric peptide library biased for hydrophilic residues was fused via flexible linker to the amino terminus of an antibody Fab fragment which bound human CD40 antigen. When ~$10^8$ members of this library were co-expressed in the *E. coli* periplasmic space with the antigen fused to the amino terminus of the BLIP-β-lactamase fusion, many peptides were obtained which supported robust growth on ampicillin concentrations which were lethal to cells not expressing the peptide or to cells expressing the peptide fused to a non-CD40-binding antibody.

Reactivators for masked or cis-quenched GFPs which can be used in systems of the present invention may be obtained in several ways. For example, a non-fluorescent GFP mutant (e.g., Ser65Ala, Heim and Tsien (1996) *Curr Biol* 6: 178-82) can be used as a reactivator. When the cis-quenched GFP and the reactivator are docked to each other by the interaction of binding ensemble members that are fused to the cis-quenched GFP and reactivator, respectively, the quencher re-equilibrates with the reactivator, and GFP fluorescence is restored. When the strain on quencher binding to GFP is greater than the strain on quencher binding to the reactivator, the equilibrium will shift toward the latter, and interaction-mediated GFP reactivation can go to near completion. GFP reactivators can also be isolated from antibody, immunoglobulin variable region, or scaffolded peptide libraries using the methods of the present invention. For example, the cis-quenched GFP and a library of binding molecules such as trxpeps can each be fused to binding ensemble members. When co-expressed in *E. coli* cells and plated on solid medium, useful reactivators can be identified and isolated by screening the resultant colonies for fluorescence at the wild-type GFP maxima.

Binding Ensemble Members

Binding ensemble members for most applications will be two or more protein molecules or stable fragments thereof which interact with one another. For many applications the binding ensemble members may comprise binding pairs from recognizable classes, such as receptor/ligand pairs or antigen/antibody pairs. For other applications the binding ensemble members may comprise subunits of higher order structures such as multi-subunit enzymes or other functional protein assemblies of the cell, such as those responsible for cytoskeletal or nuclear architecture. The binding ensemble members may also include proteins or stable fragments thereof that interact transiently or temporally in such intracellular processes as signal transduction, gene expression, and metabolism. For example, many transcription factors have multiple subunits, such as the c-fos and c-jun subunits of AP-1 (Karin et al. (1997) *Curr Opin Cell Biol* 9: 240-6). For still other applications, the binding ensemble members may comprise combinations of proteins of interest with one or two additional binding proteins or domains, which provide additional docking functions. For example, an ensemble might comprise three molecules where the first and second molecules are complexed with the responder and reactivator, respectively, and the third molecule binds to the first and second molecules (and the first and second molecules do not bind to each other). Alternatively, an ensemble might comprise a bait protein (fused to the responder), and a pair of docking domains, such as leucine zipper helixes, fused to an expressed sequence library and the reactivator, respectively. Binding proteins or domains may include antibody fragments, peptides, scaffolded peptides, or immunoglobulin variable region domains, which have been selected from diverse natural or artificial populations for their ability to bind to the proteins of interest.

Many applications will involve the use of unmodified target molecules to dock the components of the system. Such applications include detection of analytes in clinical, biological, manufactured, or environmental specimens; detection of cell surface molecules for e.g., prodrug activation; and mapping the epitopes of target molecules. Such applications typically use two binding molecules which bind non-overlapping epitopes on the target molecule, or which bind to each other only in the presence of the target molecule. One binding molecule is linked to the responder-inhibitor fusion, and the other is linked to the reactivator, such that only in the presence of the free target molecule is the responder-inhibitor fusion docked to the reactivator, thereby activating the responder.

Non-protein subject molecules can also be used. For example, small molecules such as hormones (e.g., steroids), vitamins, nutrients (e.g., sugars), or toxins (e.g., anthracyclines), or small molecules selected from small molecule/combinatorial libraries (e.g., the libraries recited in the section on inhibitors) can be used as binding ensemble members in vitro. When the system is deployed in cells, small subject molecules may be used by conjugating them to a chemical tag such as biotin. Such conjugates typically can diffuse freely into the bacterial periplasm, allowing them to serve, for example, as antigens for antibody selection using the β-lactamase/BLIP/BIP system. An antibody library is linked to either the β-lactamase-BLIP fusion or to BIP, and a binder to the chemical tag, such as streptavidin, is linked to the other component. Antibodies that bind the small subject molecule are selected by their ability to activate β-lactamase, thereby conferring antibiotic resistance on the cells.

Further examples of subject molecules are found in U.S. Pat. Nos. 6,294,330; 6,220,964; 6,342,345; and/or U.S. patent application Ser. No. 09/526,106, filed on Mar. 15, 2000, which are hereby incorporated by reference.

Affinity Considerations

In a preferred embodiment of the invention the binding of inhibitor to responder must be of relatively low affinity, i.e., stable enough to maintain the responder in the inactive state, but sufficiently unstable that it can readily be displaced by the reactivator when the latter is docked to the responder complex by the interaction of binding ensemble members. Further, the affinity of the responder-inhibitor interaction must be high enough to prohibit reactivation in the absence of binding ensemble interaction at working concentrations. These conditions are generally satisfied by a combination of two effects, a concentration effect and a strain effect. The concentration effect reflects the fact that tethered molecules typically have 1000-fold higher concentration relative to one another than the working concentrations of the molecules. For example, tethered proteins typically have the equivalent of millimolar concentrations relative to one another, but are present in cells or are used in vitro at concentrations of micromolar or less. Thus, a $K_d$ in the sub-millimolar range should satisfy the concentration effect condition for an optimally reactivatable responder-inhibitor fusion.

The natural affinity of BLIP for β-lactamase is in the nanomolar range (Strynadka et al., (1994) *Nature* 368: 657-660), and so the latter is difficult to reactivate when the two are fused together. However, mutations may be introduced into β-lactamase at Glu104 (to Lys, Gln, Asp, or Ala), or into BLIP at Asp 149 (to Ala) or at Phe142 (to Ala) that reduce the affinity without appreciable effect on stability or on the enzymatic activity of β-lactamase. Thus, when fused to BLIP, a low-affinity β-lactamase Glu104 (E104) mutant can be fully reactivated by the high-affinity wild-type BIP, or by BLIP-F142A, which binds β-lactamase but does not inhibit (Petrosino et al., (1999) *J Biol Chem* 274:2394-2400), when they are docked together by a subject protein interaction. Similarly, when fused to BLIP-D49A, wild-type β-lactamase can be fully reactivated by interaction-mediated docking to BIP or BLIP-F142A. A further reduction in affinity between linked β-lactamase and BLIP, or between any linked responder and its inhibitor, may result from the strain effect. The strain effect reflects the fact that, depending on the length and stiffness of the linker, tethered proteins typically have restricted freedom of movement relative to one another, so that the association rate component of affinity is lower than it would be if the proteins were not fused, i.e., had complete freedom of movement, at the same concentration. Further, the linked proteins may also be under tortional strain when bound to one another, and this would increase the dissociation rate component of affinity.

This strain effect allows the affinity of the responder-inhibitor interaction to be modulated to some extent by adjusting the length of the linker. For example, it is useful for the responder-inhibitor interaction to have a higher dissociation rate constant ($k_d$) than that of the bound complex of binding ensemble members, so that when the responder-inhibitor fusion is docked to the reactivator by interaction between the subject binding ensemble members, the reactivator has time to bind to the inhibitor before the binding ensemble proteins disengage. Since subject protein interactions will typically have $k_d$s in the range of $10^{-3}$ sec$^{-1}$ or lower, it is useful for the responder-inhibitor $k_d$ to be higher than this value. One way in which the $k_d$ of a fused responder-inhibitor complex may be increased is to shorten the linker between them, thereby increasing the torsional strain. For example, when the linker between wild-type β-lactamase and BLIP is 15 amino acid residues in length (e.g., (Gly$_4$Ser)$_3$) β-lactamase is fully inhibited, but the tortional strain on the complex is such that the enzyme can be fully activated when the complex is docked to BIP by a subject protein interaction, even though both BIP and β-lactamase have the same affinity for BLIP. This suggests that the BIP-BLIP interaction in the docked complex is under much less strain than the β-lactamase-BLIP interaction, so that the equilibrium is shifted far toward the latter interaction. This conclusion is supported by molecular modeling from the x-ray crystal structure of the β-lactamase-BLIP complex (Strynadka, et al., (2001) *Nat. Struct. Biol.* 8:848ff), which shows that a 15-mer linker is too short to permit a fully relaxed complex, but comparable linkers from the subject proteins to β-lactamase/BLIP and to BIP are more than long enough to permit a relaxed complex of BIP and BLIP.

Figure 4:
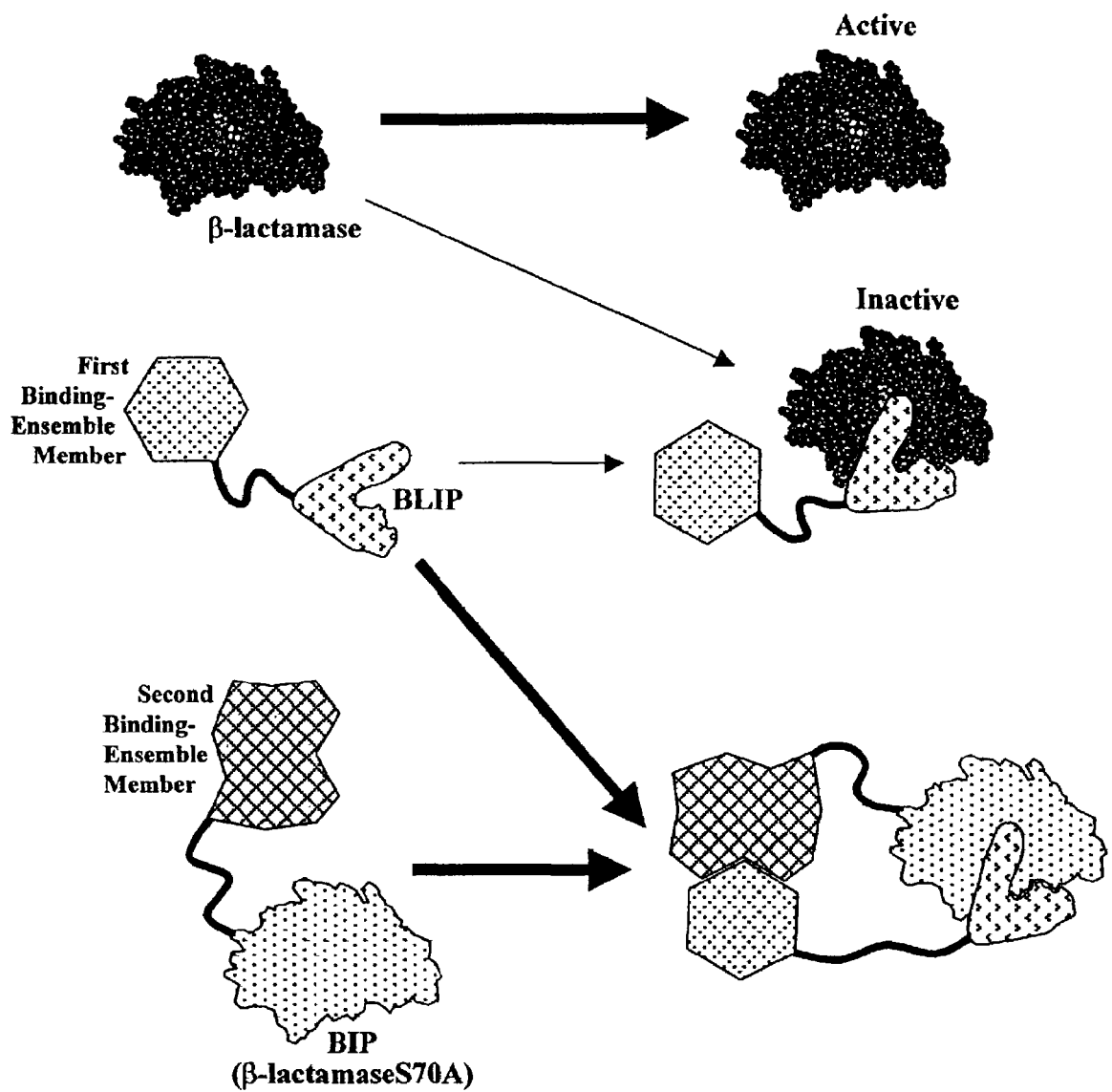
FIG. 4 illustrates an embodiment in which free wild-type β-lactamase is constitutively inhibited by wild-type BLIP fused to a first binding ensemble member, except when the first binding ensemble member interacts with other members of the ensemble, at least one of which is fused to a reactivator, in this case BIP.

In another embodiment, the responder molecule is unlinked and the inhibitor and reactivator are each linked to a first and second subject molecule, such that when the subject molecules interact, the reactivator is docked to the inhibitor, preventing the inhibitor from binding to the responder, and thereby activating the latter (see, e.g, FIG. 4). In this embodiment a high-affinity interaction between responder and inhibitor is necessary to ensure that the responder is maximally inhibited at working concentrations in the absence of a subject molecule interaction.

The affinity of the reactivator for the inhibitor must be lower, so that it does not bind to the inhibitor at working concentrations in the absence of a subject molecule interaction. Thus, when the $K_d$ of the inhibitor and the responder is ten-fold below the working concentrations of both, and 100-fold below the $K_d$ of the inhibitor and the reactivator, and the working concentrations are at least 1000-fold below the effective mutual concentrations of inhibitor and reactivator when docked to one another, a subject interaction with a $K_d$ comparable to that of the responder-inhibitor interaction would be capable of driving the bulk of the responder from >90% inhibited to >90% activated. Such a result can be obtained with the following conditions: (1) working concentrations of the components in the micromolar range, as when stably expressed in cells, (2) a modest $K_d$ of ~0.1 μM for both the responder-inhibitor interaction and for the subject molecule interaction, (3) a $K_d$ of ~10 μM for the inhibitor-reactivator interaction, and (4) an effective mutual concentration in the millimolar range for the inhibitor and reactivator when docked together.

Generation of Conjugate Molecules

The responder-inhibitor and reactivator conjugates can be joined by methods well known to those of skill in the art. These methods include both chemical and recombinant means.

Chemical means of joining the heterologous domains are described, e.g., in *Bioconjugate Techniques*, Hermanson, Ed., Academic Press (1996). These include, for example, derivitization for the purpose of linking the moieties to each other, either directly or through a linking compound, by methods that are well known in the art of protein chemistry. For example, in one chemical conjugation embodiment, the means of linking responder-inhibitor fusion, and the reactivator molecules to the subject molecules comprises a heterobifuncitonal coupling reagent that ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide bond can be formed between cysteine residues present in each of the protein molecules to be linked. The cysteines can occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

The means of linking the heterologous domains of the protein can also comprise a peptidyl bond formed between domains that are separately synthesized by standard peptide synthesis chemistry or recombinant means. The protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) *J. Am. Chem. Soc.*, 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, *Proteins Structures and Molecular Principles*, 50-60 (1983)). The composition of the synthetic polypeptides or of subfragments of the polypeptide, may be confirmed by amino acid analysis or sequencing (e.g., the Edman degradation procedure; see Creighton, *Proteins, Structures and Molecular Principles*, pp. 34-49 (1983)).

In some embodiments, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, α-Abu, α-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, α-alanine, fluoro-amino acids, designer amino acids such as α-methyl amino acids, Cα-methyl amino acids, Nα-methyl amino acids, and amino acid analogs in general. Furthermore, the amino acid can be D (dextrorotary) or L (levorotary).

In another embodiment, the responder-inhibitor and reactivator conjugates, are joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similar linking group.

In a specific embodiment, the coding sequences of each polypeptide in the fusion protein are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that can interact with functional epitopes on the first and second polypeptides; and (3) the lack of hydrophobic or charged residues that might react with the polypeptide functional epitopes. Typical peptide linker sequences contain Gly, Val and Thr residues. Other near neutral amino acids, such as Ser and Ala can also be used in the linker sequence. Amino acid sequences which may be usefully employed as linkers include those disclosed in Maratea et al. (1985) Gene 40:39-46; Murphy et al. (1986) *Proc. Natl. Acad. Sci. USA* 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterofunctional linkages.

Other methods of joining the components of the responder, inhibitor and reactivator conjugates include ionic binding by expressing negative and positive tails, and indirect binding through antibodies and streptavidin-biotin interactions. (See, e.g., *Bioconjugate Techniques*, supra). The components can also be joined together through an intermediate interacting sequence. The moieties included in the conjugate molecules can be joined in any order, and the most favorable order is generally determined empirically to be that which produces the least steric impediment to responder reactivation upon the interaction of subject molecules which are linked or conjugated to the responder and the reactivator.

In one embodiment, a plurality of putative binding ensemble members are bound to their respective complex (either responder or reactivator) through the interaction of a pair of other binding ensemble, such as for example, antibody/antigen, receptor/ligands, biotin/avidin, c-fos/c-jun, and interacting protein domains such as leucine zippers and the like. One member of the interaction pair is linked to the appropriate complex (either responder or reactivator) and a plurality of the other is linked individually to a plurality of putative binding ensemble members. The plurality of putative binding ensemble members can then be docked to the appropriate complex by the binding of the interaction pair.

The interaction pairs of the above embodiment can be used to generate a plurality of putative binding ensemble members in vivo. This is done by using a vector (e.g., a transposon or viral based vector) that will insert into the host cell DNA and tag the proteins encoded in that DNA with one of the interaction pairs (e.g., c-fos). The appropriate complex is then placed into these tagged cells to make the plurality of complex (responder or reactivator) bound individually to the plurality of putative binding ensemble members. The tags will also be useful for identifying and obtaining the genes from the plurality of putative binding member clones that are positive in the interaction assay. Alternatively, the plurality of putative binding ensemble members can be constructed by cloning random DNA fragments from suitable DNA and inserting these fragments into an expression vector so that the inserted DNA fragments will encode a protein that is fused to one member of the interaction pair. Examples of methods for generating tagged libraries for these embodiment are disclosed in Telmer et al. (2002) *Biotechniques* 32(2):422-24; Uzzau et al. (2001) *Proc. Nat'l Acad. Sci.* 98(26):15264-29; Chuang et al. (2001) *J. Biomed. Sci.* 8(2):170-75; Kempken and Windhofer (2001) *Chromosoma* 110(1): 1-9; Belmont (2001) *Trends Cell. Biol.* 11(6):250-57; Hadjantonakis and Nagy (2001) *Histochem. Cell. Biol.* 115(1):49-58; Harrington et al. (2001) *Nat. Biotechnol.* 19(5):440-45; Cecconi and Meyer (2000) *FEBS Lett.* 480(1):63-71; Chapman-Smith and Cronan (1999) *Biomol. Eng.* 16(1-4):119-25; Jarvik Jarvik and Telmer (1998) *Ann. Rev. Genet.* 32:601-18; Misteli and Spector (1997) *Nat. Biotechnol.* 15(10):961-64; Smith (1997) *Biotechniques* 23(1):116-20, which are hereby incorporated by reference.

Production of Proteins Using Recombinant Techniques

Often, the responder, inhibitor, and reactivator conjugates included in the systems of the invention are protein molecules that are produced by recombinant expression of nucleic acids encoding the proteins as a fusion protein. Expression methodology is well known to those of skill in the art. Such a fusion product can be made by ligating the appropriate nucleic acid sequences encoding the desired amino acid sequences to each other by methods known in the art, in the proper reading frame, and expressing the product by methods known in the art (see, e.g., Scopes, *Protein Purification: Principles and Practice*, Springer-Verlag, N.Y. 1994; Sambrook and Russell, eds, *Molecular Cloning: A Laboratory Manual*, 3rd Ed, vols. 1-3, Cold Spring Harbor Laboratory Press, 2001; and *Current Protocols in Molecular Biology*, Ausubel, ed. John Wiley & Sons, Inc. N.Y., 1997).

Nucleic acids encoding the domains to be incorporated into the fusion proteins of the invention can be obtained using routine techniques in the field of recombinant genetics (see, e.g., Sambrook and Russell, eds, *Molecular Cloning: A Laboratory Manual*, 3rd Ed, vols. 1-3, Cold Spring Harbor Laboratory Press, 2001; and *Current Protocols in Molecular Biology*, Ausubel, ed. John Wiley & Sons, Inc. N.Y., 1997).

Often, the nucleic acid sequences encoding the component domains to be incorporated into the fusion protein are cloned from cDNA and genomic DNA libraries by hybridization with probes, or isolated using amplification techniques with oligonucleotide primers. Amplification techniques can be used to amplify and isolate sequences from DNA or RNA (see, e.g., Dieffenbach & Dveksler, *PCR Primers: A Laboratory Manual* (1995)). Alternatively, overlapping oligonucleotides can be produced synthetically and joined to produce one or more of the domains. Nucleic acids encoding the component domains can also be isolated from expression libraries using antibodies as probes.

In an example of obtaining a nucleic acid encoding a domain to be included in the conjugate molecule using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be easily ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Examples of techniques sufficient to direct persons of skill through in vitro amplification methods are found in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

In some embodiments, it may be desirable to modify the polypeptides encoding the components of the conjugate molecules. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81-97, Roberts et al. (1987) *Nature* 328: 731-734.

For example, the domains can be modified to facilitate the linkage of the two domains to obtain the polynucleotides that encode the fusion polypeptides of the invention. Catalytic domains and binding domains that are modified by such methods are also part of the invention. For example, a codon for a cysteine residue can be placed at either end of a domain so that the domain can be linked by, for example, a disulfide linkage. The modification can be performed using either recombinant or chemical methods (see, e.g., Pierce Chemical Co. catalog, Rockford Ill.).

The domains of the recombinant fusion proteins are often joined by linkers, usually polypeptide sequences of neutral amino acids such as serine or glycine, that can be of varying lengths, for example, about 200 amino acids or more in length, with 1 to 100 amino acids being typical. Often, the linkers are 10, 15, 20, 25, 30, 35, 40, 45, or 50 amino acid residues or less in length. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art. Typically, a flexible linker is a peptide linker of any length whose amino acid composition is rich in glycine to minimize the formation of rigid structure by interaction of amino acid side chains with each other or with the polypeptide backbone. A typical flexible linker has the composition $(Gly_4Ser)_x$.

In some embodiments, the recombinant nucleic acids encoding the fusion proteins of the invention are modified to provide preferred codons which enhance translation of the nucleic acid in a selected organism (e.g., yeast preferred codons are substituted into a coding nucleic acid for expression in yeast).

Expression Cassettes and Host Cells for Expressing the Fusion Polypeptides

There are many expression systems for producing the fusion polypeptide that are well know to those of ordinary skill in the art. (See, e.g., *Gene Expression Systems*, Fernandes and Hoeffler, Eds. Academic Press, 1999.) Typically, the polynucleotide that encodes the fusion polypeptide is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites, enhancers, operators, and the like are also optionally included. Constructs that include one or more of these control sequences are termed "expression cassettes." Accordingly, the nucleic acids that encode the joined polypeptides are incorporated for the desired level of expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) δ: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, pET23D, λ-phage derived vectors, p15A-based vectors (Rose, *Nucleic Acids Res.* (1988) 16:355 and 356) and fusion expression systems such as GST and LacZ. Epitope tags can also be added to recombinant proteins to provide convenient methods of isolation, e.g., c-myc, HA-tag, 6-His tag, maltose binding protein, VSV-G tag, anti-DYKDDDDK tag, or any such tag, a large number of which are well known to those of skill in the art.

For expression of fusion polypeptides in prokaryotic cells other than *E. coli*, regulatory sequences for transcription and translation that function in the particular prokaryotic species is required. Such promoters can be obtained from genes that have been cloned from the species, or heterologous promoters can be used. For example, the hybrid trp-lac promoter functions in *Bacillus* in addition to *E. coli*. These and other suitable bacterial promoters are well known in the art and are described, e.g., in Sambrook et al. and Ausubel et al. Bacterial expression systems for expressing the proteins of the invention are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available.

Similarly, for expression of fusion polypeptides in eukaryotic cells, transcription and translation sequences that function in the particular eukaryotic species are required. For example, eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the concentration of heterologous protein in the host cell can be controlled. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra.

Inducible promoters for other organisms are also well known to those of skill in the art. These include, for example, the metallothionein promoter, the heat shock promoter, as well as many others.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

In some embodiments it may be desirable to include a signal peptide to target the expressed product to a particular location, e.g., a bacterial periplasmic space. Such signal polypeptides are known in the art.

The construction of polynucleotide constructs generally requires the use of vectors able to replicate in host bacterial cells, or able to integrate into the genome of host bacterial cells. Such vectors are commonly used in the art. A plethora of kits are commercially available for the purification of plasmids from bacteria (for example, EasyPrepJ, FlexiPrepj, from Pharmacia Biotech; StrataCleanJ, from Stratagene; and, QIAexpress Expression System, Qiagen). The isolated and purified plasmids can then be further manipulated to produce other plasmids, and used to transform cells.

The fusion polypeptides can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., *Bio/Technology* (1984) 2: 800; Schoner et al., *Bio/Technology* (1985) 3: 151). Fusion polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the recombinant fusion polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 90 to 95% homogeneity are preferred, and 98 to 99% or more homogeneity are most preferred.

To facilitate purification of the fusion polypeptides of the invention, the nucleic acids that encode the fusion polypeptides can also include a coding sequence for an epitope or "tag" for which an affinity binding reagent is available. Examples of suitable epitopes include the myc and V-5 responder genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, N.Y.; commercially available from Qiagen (Santa Clarita, Calif.)).

One of skill would recognize that modifications can be made to the protein domains without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences Modification of polypeptide domains to produce variants may also be performed. A "variant" has used herein refers to a version of the polypeptide of interest that has been mutated. Typically, a population of variants is produced in order to select a version of the polypeptide of interest that has an enhanced property relative to the parent, e.g., increased binding affinity. Thus, a variant specifically binds the same binding partner as the parent binding pair member. Methods of introducing mutations are well known in the art (see, e.g., Sambrook and Ausubel, supra). For example, error-prone PCR or chemical mutagenesis can be performed to introduce mutations. In some embodiments, it may be desirable to introduce mutations at particular sites and then select for the enhanced property. In such instances, techniques such as site-specific mutagenesis may be performed.

Applications of the Invention

The methods and systems of the invention have many applications for which they offer distinct advantages over existing molecular interaction-sensing technologies such as two-hybrid systems and fragment or subunit complementation systems. These applications include but are not limited to the following: (1) selection of antibodies and other binding molecules for antigens of interest, (2) affinity maturation of antibodies and other binding molecules, (3) protein-protein interaction mapping for functional proteomics, (4) analyte detection assays for clinical diagnostics, expression profiling, food testing, environmental testing, and process monitoring, (5) high-throughput cell-based screening systems for agonists and antagonists of signal transduction pathways involved in disease, and (6) target-mediated activation of prodrugs and other therapeutic or diagnostic reagents at specific locations in the body. All the methods for selecting/screening for binding ensemble members (e.g., improved binding members or novel binding members) employ at least one round of selection/screening, and may include additional rounds of selection/screening.

U.S. Pat. Nos. 6,342,345, 6,294,330, and 6,270,964, and/or U.S. patent application Ser. No. 09/562,106, filed Mar. 15, 2000, disclose applications for fragment based complementation systems that can be adapted to the whole enzyme reactivation systems of the invention. These patents and this patent application are hereby incorporated by reference.

Selection of Antibodies and Other Binding Molecules

The methods and systems of the invention may be used for the selection of antibodies and other binding molecules which bind with high affinity and specificity to molecules of interest, or "antigens". In one embodiment the antigen is linked to a responder-inhibitor fusion and the binding molecule library is linked to a reactivator molecule. Alternatively, the antigen may be linked to the reactivator, and the binding molecule library is linked to the responder-inhibitor fusion. Gene expression constructs for both fusion molecules are then introduced into a suitable cell line such that all cells express the antigen fusion and each cell expresses at least one binding molecule library member. The doubly-transformed cells are then screened for the phenotype conferred by the responder. Only cells which express binding molecule library members which bind specifically to the antigen, thereby docking the reactivator to the responder and activating the latter, will exhibit the selectable phenotype, allowing the antigen-specific binding molecule to be isolated.

In many applications it is desirable to obtain binding molecules for multiple epitopes on an antigen. For example, binding to a specific epitope on a cell surface receptor may be required for a desired biological activity in a therapeutic application, but the required epitope often is not known. Thus, binding molecules for multiple epitopes may need to be tested to find the desired bioactivity. This is the principal reason for failure of many attempts to develop therapeutic antibodies, because most antibody selection methods have strong epitope biases, which may exclude the required epitopes. For example, the antibody responses of most animals to foreign antigen exhibit strong epitope biases, which are indifferent to required target epitopes for desired bioactivities. Likewise, in vitro methods such panning of phage displayed antibody libraries against immobilized antigens have strong epitope biases because protein antigens typically denature when attached to non-biological surfaces, thus native epitopes are often lost or obscured. Antigen-specific binding molecules selected with some embodiments of the invention are also likely to be restricted with respect to the epitopes they bind on the antigen because binding to some epitopes may orient the reactivator in such a way that the responder-inhibitor complex is sterically inaccessible to it, thus binders to such epitopes may not be selectable.

However, the above-described epitope restriction may be overcome using another embodiment of the invention. In this embodiment, the antigen is subjected to a second round of selection in which the binding molecules selected in the first round replace the antigen as the fusion partner of the responder-inhibitor or the reactivator, whichever was originally used. The antigen is expressed free. These molecules are then co-expressed in the same host cells with the original binding molecule fusion library, such that each cell now expresses the free antigen with one or more first antigen-binding molecules fused to one responder activation component, and one or more binding molecule library members fused to the other responder activation component. Cells which express an antigen-binder from the library in addition to a first antigen binder, and in which simultaneous binding of both antigen-binders to the antigen productively docks the reactivator to the cis-inhibited responder, thereby activating the responder, will express the selectable phenotype. It should be noted that in this selection round each epitope of the antigen is presented to the binding molecule library in multiple orientations, determined by the different epitopes bound by the first antigen-binders. Thus, epitopes which failed to support productive reactivator docking when bound by an antigen-binder in the first round of selection may do so in the second round when the epitope orientation is varied. This process may be repeated in a third round of selection, if desired, especially for large antigens, to ensure that high-affinity binders have been obtained for all interaction-competent epitopes on the antigen in its native conformation.

An example of this application is the isolation of human antibody scFv fragments that bind specifically to a model antigen using *E. coli* cells expressing β-lactamase as the responder fused to its natural inhibitor BLIP, and a disabled β-lactamase mutant, BIP, as the reactivator. In one embodiment the antigen is fused via flexible linker (e.g., $(Gly_4Ser)_3$) to the amino terminus of BLIP, which is fused in turn via similar linker to the amino terminus of β-lactamase. The antigen has a signal peptide sequence at its amino terminus to facilitate translocation of the tripartite fusion protein across the bacterial plasma membrane into the periplasmic space, where β-lactamase activity is required for antibiotic resistance. The β-lactamase-BLIP affinity is reduced by virtue of a D49A mutation in BLIP, and/or by an E104K, D, Q, or A mutation in β-lactamase, and/or by linker-induced strain, so that the enzyme is fully inhibited in cis, but can be readily reactivated when docked to BIP by an antigen-antibody interaction. A vector for expression of the gene for this tripartite fusion protein is illustrated in FIG. 5, and may be constructed by using techniques standard in the art (see, e.g., Sambrook and Russell, eds, *Molecular Cloning: A Laboratory Manual,* 3rd Ed, vols. 1-3, Cold Spring Harbor Laboratory Press, 2001; and *Current Protocols in Molecular Biology*, Ausubel, ed. John Wiley & Sons, Inc. N.Y., 1997).

A human non-immune antibody repertoire library may be assembled in single chain Fv format as described in the art (see, e.g., Marks et al., (1991) *J. Mol Biol* 222:581-97). Routinely, such libraries can have $10^9$ or more distinct binding specificities. The coding sequences for this antibody scFv library are recovered by PCR and subcloned for expression as fusions via flexible linker to the amino terminus of BIP. The scFvs have signal peptides at their amino termini for translocation to the periplasmic space. A vector for expression of these fusion proteins, which is compatible with the tripartite fusion protein expression vector, is illustrated in FIG. 5, and may be constructed using techniques common in the art. This vector may be a phagemid vector which comprises both plasmid and bacteriophage origins of replication, and by virtue of the latter, can be encapsulated in phage particles and recovered as such from cells infected with helper phage (see, e.g., Sambrook and Russell, supra). The resulting large phagemid library can then be introduced efficiently into cells expressing the tripartite antigen fusion by high-mulitplicity transfection. Each transfected cell will then express the tripartite antigen fusion and usually one antibody scFv-BIP fusion. The reactivation of BLIP-inhibited β-lactamase by BIP when docked by the interaction of a model antibody scFv with a model antigen is illustrated using x-ray crystal structures in FIG. 6.

With an scFv library of ~$10^9$ members it is desirable to transfect at least $10^{11}$ cells, so that at least $10^{10}$ can be plated on each of several concentrations of antibiotic. The minimum antibiotic concentration for clean selection is established with a pilot transfection in which only a small aliquot of the library is transfected and plated on a series of antibiotic concentrations. The aliquot is small enough not to contain any antigen binders, but large enough to be statistically significant, e.g., 100-1000 clones. Typically, one might wish to recover antibodies that confer at least a 1000-fold or 10,000-fold increase in plating efficiency (i.e., percentage of cells producing colonies), in which case selection is begun using that concentration of antibiotic on which the pilot transfection plated with an efficiency of 0.1% -0.01%. As the frequency of selectable antigen binders is typically lower than this, colonies recovered from the lowest concentrations are usually heavily contaminated with low-plating efficiency background colonies, and are therefore replated several times at no more than ~10 cells per colony to eliminate the background colonies. Colonies appearing on higher antibiotic concentrations where the background plating efficiencies are lower, will require fewer replatings, or even none, to eliminate the background colonies. Typically the antigen specificity of thus-selected antibody scFvs is then confirmed by rescuing the scFv-expressing phagemids, retransfecting each in the absence of antigen, and subjecting supernatants of overnight suspension cultures of cells expressing each antibody scFv clone to antibody capture ELISA using purified, immobilized antigen.

As discussed above, depending on the size of the antigen, all available epitopes on the antigen may not be represented in the recovered panel of antigen-binding scFvs because in the present embodiment the locations of some epitopes may orient binding scFv-BIP fusions in such as way that BIP does not have adequate access to the BLIP-β-lactamase fusion. To obtain antibody scFvs to such excluded epitopes, the original panel of antigen-specific scFvs can be used to re-orient the antigen with respect to the library so that the presentation of these epitopes is more favorable for responder reactivation. This is accomplished by fusing the first panel of antigen-binding scFvs to the β-lactamase-BLIP fusion, and co-expressing these with the free antigen and the original library of scFv-BIP fusions (see, e.g., FIG. 5B), such that each transfected cell now expresses the free antigen with one of the originally-selected binders and one member of the scFv library. Anchorage of the antigen to the BLIP-β-lactamase fusion via the original binders effectively reverses its orientation with respect to the library, thereby maximizing exposure of previously excluded epitopes.

The second round of selection is performed essentially as described for the first round, except that the number of transfectants should be increased if possible by a factor which reflects the multiplicity of epitopes represented by the original selectants. After replating to eliminate the background, the newly-selected scFvs must be counter-screened to eliminate scFvs which activate β-lactamase by binding to something other than antigen such as the first scFv, BLIP, or β-lactamase itself. This can be readily accomplished by using an inducible promoter for the antigen, and restreaking each clone on antibiotic in the absence of inducer. Antigen-specific binders should not activate β-lactamase in the absence of antigen, and so should not restreak. Bona-fide antigen-binding scFvs are then verified as described above by antibody capture ELISA. For large antigens, the process may be repeated for a third round of selection, in the event that some epitopes are still excluded in the second round. In addition to antibody scFv fragments, examples of other binding molecules suitable for isolation and deployment suing the invention include other antibody fragments such as Fv, Fab, and variable region domains, as well as scaffolded peptides such as trxpeps.

Isotropic Binding Molecules

Isotropic binding molecules are obtained by presenting all potential binding surfaces of an ensemble member to other ensemble members or to a plurality of putative ensemble members. In one embodiment, systems for isotropic selection/screening comprise a first binding ensemble member, a prior selected/screened binding ensemble member(s), and a plurality of putative binding ensemble members from which additional binding ensemble members will be selected/screened. The prior selected/screened binding ensemble member is either one that is known to interact with the first binding ensemble member or one that was obtained in a prior round of screening/selection using the first binding ensemble member against the plurality of putative binding ensemble members.

The first binding ensemble member is subjected to additional round(s) of selection/screening in which the prior selected/screened binding ensemble members are present and the systems is placed under conditions where reactivation occurs if both the prior selected/screened binding ensemble member and a new member from the plurality of putative members bind to the first binding ensemble member. Thus, binding sites on the first binding ensemble member that did not screen/select for binding ensemble members in the prior rounds may do so in these subsequent rounds. If the prior selected/screened ensemble members are obtained from previous round(s) of selection/screening against the plurality of putative ensemble members, the prior selected/screened ensemble members must be removed from their complexes for use in the subsequent round(s) of selection/screening against the plurality of putative ensemble members.

In one embodiment, the prior selected/screened ensemble member(s) replace the first binding ensemble member in its complex and the first binding ensemble member is free in solution. The prior selected/screened ensemble member is/are then used to present the first binding ensemble member to the plurality of putative binding ensemble members that are individually complexed to a plurality of the other complex. In this way, binding ensemble members that bind to different sites on the first binding ensemble member may be obtained from the plurality of putative binding ensemble members because the putative binding members "see" the first binding ensemble member in a different orientation from the earlier round(s) of selection/screening.

In another embodiment, an additional screening/selection step is added to the method where the prior selected/screened binding ensemble member(s) is free in solution and the system is placed under conditions where the responder is reactivated only when a member of the plurality of putative binding ensemble members can bind to a site of the first binding ensemble member that does not interfere with the binding of the prior selected/screened binding ensemble member(s). This embodiment is particularly useful for selections/screenings that are done in vitro.

Analyte Detection In Vitro

One important product of the above-described process is that for each such antigen, or target molecule, one or more bi-molecular detection reagents are obtained. These reagents comprise matched pairs of target molecule-binders which can bind to the target molecule simultaneously such that when used, respectively, in a responder complex and a reactivator complex, the responder is efficiently activated to produce the desired readout in proportional response to the amount of target molecule present. Because all of the components are stable, these reagents can be deployed in vitro, and may be used in humans for therapeutic or diagnostic applications.

For example, panels of these reagents can be deployed in 2-dimensional arrays in micro-well formats for automated high-throughput profiling of the expression levels of key gene products in healthy and diseased cells and tissues both for therapeutic target identification and validation, and for clinical diagnosis. Currently the utility of such detection arrays is severely limited by the requirement for target molecule labeling, and/or by throughput limitations on existing label-free detection systems. The reagents of the present invention can be robotically dispensed in solution directly into high-density 2-dimensional arrays of micro-wells along with specimen and substrate for a sensitive colorimetric or fluorometric readout on the presence of the target antigen within minutes. No other currently available detection system has such capability. Other in vitro applications of the invention include clinical diagnostics, environmental testing, quality assurance monitoring, food testing, and manufacturing process monitoring.

Target-Mediated Reagent Activation

Systems of the invention that comprise paired target molecule-binding proteins to detect unmodified target molecules, can be directed to targets in vivo such as tumor markers to produce imageable signals at the site of an incipient tumor or other diseased tissue, or they can be used to activate cytotoxic prodrugs at such sites in the body. Indeed, β-lactamases have been used in such applications to activate cephalosporin prodrugs of anti-tumor agents such as doxorubicin and nitrogen mustards (see, e.g., Jungheim and Shepherd (1994) *Chem. Rev.* 94: 1553-66; Francisco et al., (1996) *J Immunol*, 157, 1652-8). Antibody-Directed Enzyme Prodrug Therapy (ADEPT; e.g., Bagshawe (1995) *Drug Devel Res* 34: 220-30) is a promising chemotherapeutic strategy for the treatment of cancer, in which a prodrug-activating enzyme, such as a β-lactamase, is targeted to the tumor by an antibody to which it is chemically or genetically conjugated. After unbound conjugate has cleared the circulation, an inactive prodrug, such as a cephalosporin derivative of doxorubicin, is administered, which is converted to a potent tumor-killing cytotoxin at the site of the tumor by the remaining tumor-bound enzyme. The main problem with ADEPT is that the unbound conjugate must clear the circulation before the prodrug can be administered in order to minimize systemic toxicity. However, by the time the conjugate has cleared the circulation >90% of the tumor bound enzyme has been lost (e.g., Bagshawe, 1995; Springer and Niculescu-Duvaz (1995) *Anti-Cancer Drug Design* 10: 361-72). In spite of this, ADEPT has been able to achieve higher active drug concentrations in the tumor than any other procedure (see, e.g., Sedlacek et al., in *Contributions to Oncology*, Huber and Queisser, eds. pp. 208ff Karger, Basel, 1992), and has shown promise in the clinic (Bagshawe et al., (1991) *Disease Markers* 9:233-238; Springer and Niculescu-Duvaz, 1995; Martin et al. (1997) *Cancer Chemother Pharmacol* 40: 189-201).

The reagents described herein completely obviate the unbound conjugate problem because prodrug activation can only occur at the target site, where the enzyme is activated. Thus, prodrug can be administered simultaneously with the tumor-targeting reagents to ensure the availability of maximum prodrug at the time of maximum target loading of the reagents, without regard for unbound reagents. In the same way, enzyme reactivation systems of the present invention can be targeted for activation by surface markers on other types of cells and tissues, such as pathogen-infected cells, transplants, and sites of inflammation or atherogenesis. The target-localized and activated enzymes can then be used to activate not just cytotoxins, but other types of therapeutic agents such as small molecule agonists or antagonists of biological response modifiers, as well as imaging reagents for precise localization of tissue with disease or other phenotype of interest. For example, target-activated enzymes can be used to deliver: (1) immune stimulants to tumors, (2) immuno-suppressants to sites of chronic inflammation or to organ transplants to inhibit rejection, (3) antibiotics to specific pathogens, (4) cytotoxins and antivirals to virus-infected cells, (5) hormones and other pleiotropic agents to specific cells and/or tissues, or (6) neurotransmitters and other neuro-modulators to specific nerves or tissues. Thus, target-activated enzymes can be used to deliver to any tissue any small molecule cytotoxin, hormone, steroid, prostaglandin, neurotransmitter, or agonist/antagonist of peptide hormone, cytokine, or chemokine, etc., which can be inactivated by conjugation to the appropriate substrate.

Affinity Maturation

The affinities of antibodies and other binding molecules for target molecules of interest, or "antigens", can be improved, or "matured", using methods and systems of the invention. Co-pending U.S. patent application Ser. No. 09/999,413 discloses methods and systems for the selection of higher-affinity variants of antibodies and other antigen-binding molecules by allowing each variant, or test molecule, to compete one-on-one in a transformed host cell with the parent molecule for binding to limiting amounts of the cognate antigen. The same methods as described therein can be used with responder systems of the present invention to accomplish affinity maturation essentially as described in that disclosure. The antigen would be combined to one complex of the present system, i.e., a responder complex or a reactivator complex, and a library of test molecules, e.g., mutagenic variants of the antigen-binding molecule, would be combined to the other complex. These complexes would then be co-expressed in appropriate host cells with the free parent antigen-binding molecule as the competitor, such that each cell would express the antigen fusion, the free parent binding molecule, and one of the test variants of the antigen-binding molecule fused to the other component. The parent and test binding molecules compete with each other for binding to the antigen such that the magnitude of the responder-conferred phenotype exhibited by a given cell is directly proportional to the affinity of the test variant expressed in that cell. Thus, when the cells are screened for the responder-conferred phenotype, those cells exhibiting the strongest phenotype should be expressing the highest-affinity test variants. Indeed, any cell exhibiting a phenotype which is stronger than that which would result from competition of the parent antigen-binding molecule with itself, i.e., expressed as both competitor and test molecule, should be expressing a higher-affinity test variant.

The library of test variants of the parent binding molecule can be generated using a variety of mutagenesis methods including, for example, error-prone PCR (Cadwell and Joyce, in *PCR Primer, A Laboratory Manual*, Dieffenbach and Dveksler, Eds. Cold Spring Harbor Press, Cold Spring Harbor N.Y., pp. 583-590, 1995), Parsimonious Mutagenesis (PM) (Balint and Larrick, *Gene* 137:109-118, 1993), DNA shuffling (Crameri et al., *Nature Biotechnol.* 14:315-19, 1996), random-priming recombination (RPR) (Shao et al., *Nucleic Acids Res.* 26:681-683, 1998), or the staggered extension process (StEO) (Zhao et al., *Nature Biotechnol.* 16:258-261, 1998). For these methods, except PM, it is typically desirable to have a mutation rate of 1-3 mutations per molecule to avoid unwanted mutations. For PM, higher mutation rates can be used because only the antigen combining sites of the binding molecule are mutagenized. PM may therefore be advantageous for accessing larger affinity increments. PM has additional advantages in avoiding expression mutants, avoiding immunogenicity, and in ease of sequencing.

Figure 7:
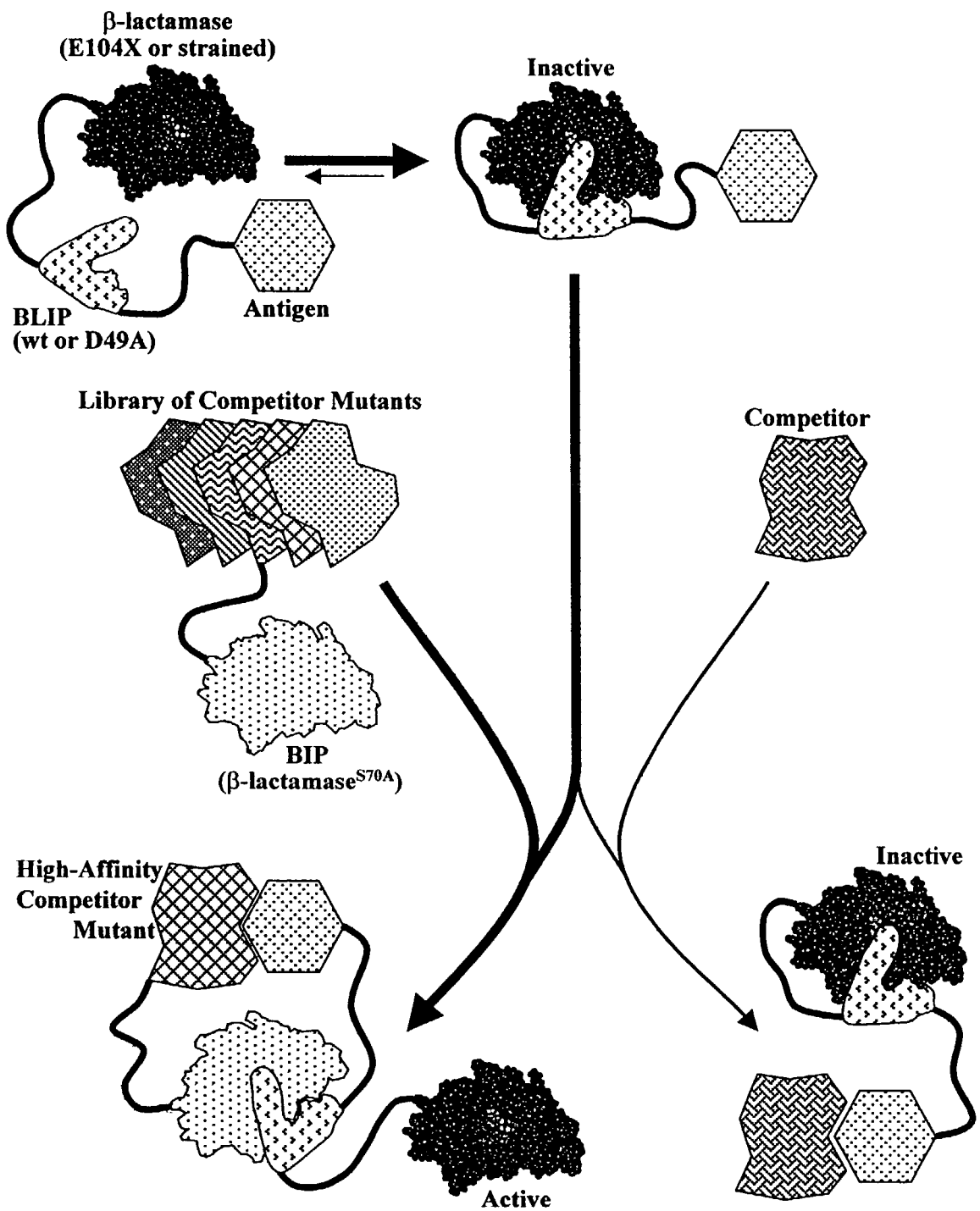
FIG. 7 is a schematic showing affinity maturation by competition for limiting antigen using a β-lactamase reactivation system of the present invention. The molecule of interest, i.e., the antigen, linked to the amino terminus of the BLIP-β-lactamase fusion, is co-expressed in *E. coli* cells with (a) a molecule which binds to the antigen ("competitor"), such as an antibody, and (b) a library of mutants of the competitor, linked to the amino terminus of the reactivator, in this case, BIP. The cells are then selected for growth in the presence of antibiotic at a concentration which is lethal for cells expressing the same binder as both the competitor and the reactivator fusion. Thus, only cells expressing a variant of the competitor which has a higher affinity for the antigen, allowing more β-lactamase to become reactivated (indicated by the thicker arrow), will be able to grow in the presence of the antibiotic.
Figure 8:
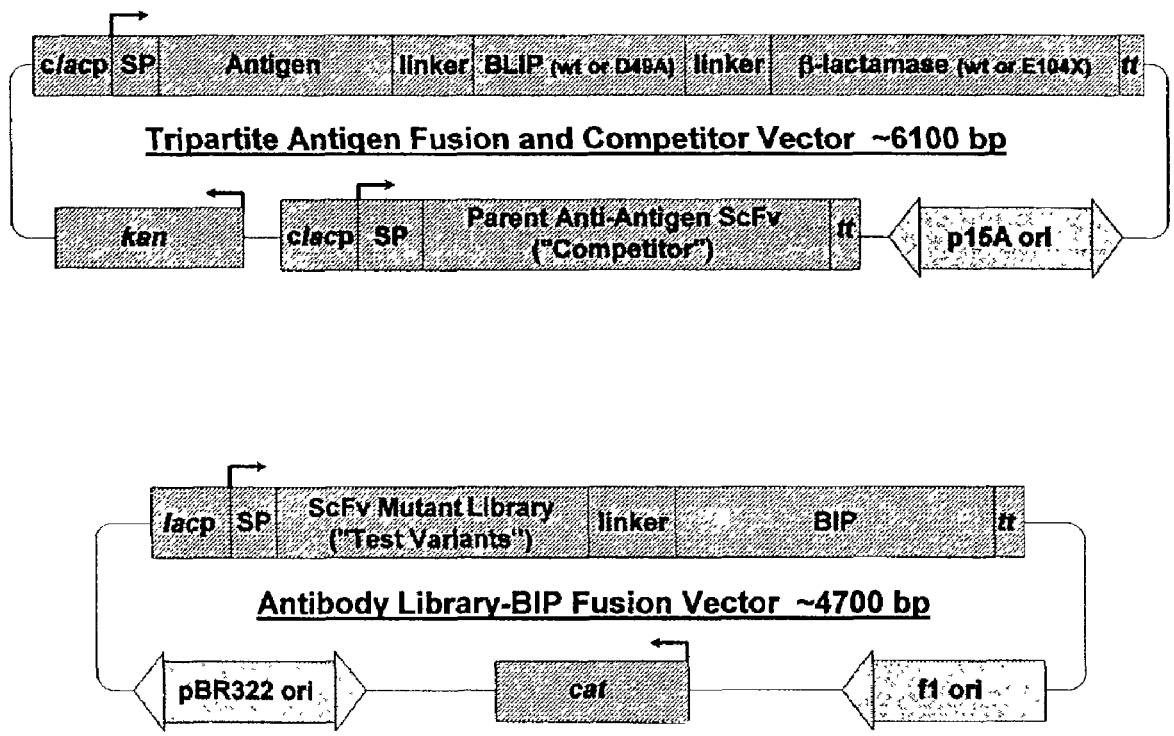
FIG. 8 shows exemplary vectors for affinity maturation of an antibody scFv fragment by competition for limiting antigen using a β-lactamase reactivation system of the present invention. As in FIG. 7, the antigen is linked to the amino terminus of the BLIP-k β-lactamase fusion and library of "test variants" of the antigen-binding scFv is fused to the reactivator, while the scFv "competitor" is expressed from a separate vector. Abbreviations are defined in the description of FIG. 5.

Affinity maturation of an antibody is illustrated in FIG. 7 for an embodiment of the invention that uses *E. coli* cells expressing β-lactamase as the responder fused to BLIP, and expressing BIP as the reactivator. In this example, the antigen is fused, via $(Gly_4Ser)_3$ linker, to the amino terminus of BLIP, which is in turn fused via a similar linker to the amino terminus of β-lactamase. The β-lactamase—BLIP affinity is reduced by virtue of a D49A mutation in BLIP, and/or by an E104K, D, Q, or A mutation in β-lactamase, and/or by linker-induced strain, so that the enzyme is fully inhibited in cis, but can be readily reactivated when docked to BIP by the antigen-antibody interaction. In the same *E. coli* cells, the parent antibody is expressed free as the competitor, and a population of mutagenic variants of this antibody is expressed as the test molecule library fused to the amino-terminus of BIP, such that each cell expresses one test variant along with the competitor fusion and the tripartite antigen fusion. All three components also comprise amino terminal signal peptides for their translocation into the periplasmic space. Vectors for expression of these components can be constructed using standard art, and are illustrated in FIG. 8. It is convenient to use a phagemid vector for the test variant library to allow facile recovery of selected variants for further testing.

Selection of higher-affinity variants is accomplished by plating the cells onto solid medium containing a β-lactam antibiotic such as ampicillin at a concentration which is lethal for cells expressing the parent antibody competing against itself, i.e., as both competitor and test molecule. The optimal antibiotic concentration is typically one on which cells expressing the parent antibody as test molecule plate with <1% efficiency, i.e., produce fewer than one colony per 100 cells plated. Under these conditions variants with higher plating efficiencies (>10%) can be readily isolated by several rounds of replating at no more than about 10 cells per colony, in the course of which all unimproved test molecules are eliminated. Selection for β-lactamase-dependent antibiotic resistance has an advantage for affinity maturation in that the relationship between enzyme activity and antibiotic resistance is highly non-linear, such that small increments in affinity, leading to small increments in β-lactamase activity, can produce much larger increments in plating efficiency at the critical point in the antibiotic concentration curve.

Some variants may be selected by virtue of higher stability or expression levels rather than by higher affinity. This is less likely when mutagenesis is targeted to the surface loops of the molecule which interact with antigen, as in the PM technique, rather than to the whole molecule. Expression variants can be detected by western blotting (an epitope tag is present on the carboxyl terminus of BIP for detection with anti-tag antibody), and then comparing the intensity of each selected variant-BIP fusion with that of the parent scFv-BIP fusion under the same conditions. Affinities of selected antibodies can be measured by established methods in the art, such as competition ELISA (e.g., Harlow and Lane, *Antibodies A Laboratory Manual*, Cold Spring Harbor Laboratory Press, 1988) and surface plasmon resonance (e.g., Fägerstam et al. (1992) *J Chromatog* 597: 397-410). Expression mutants may nevertheless be desirable, and such mutants may be used as competitors in subsequent rounds of selection for higher-affinity variants, in which selection of additional stability/expression mutants is less likely. This process of affinity maturation should be repeated, with each successive higher-affinity variant being expressed as the competitor in the next round, and also being mutagenized to produce the test variant library for the next round, until no further increments in affinity can be achieved.

Protein-Protein Interaction Mapping

Systems and methods of the invention may also be used to identify natural interactions among the gene products of the human proteome, such as those interactions which comprise the operational circuitry of such fundamental cellular processes as signal transduction, the cell division cycle, gene expression, and the regulation of metabolism. The most successful current method for identifying natural ligands of proteins of interest from expressed sequence libraries is the yeast two-hybrid system (see, e.g., Fields and Song, *Nature* 340:245-247 (1989); Chien et al., *Proc. Natl. Acad. Sci.* (*USA*) 88:9578-9582 (1991)). In this method the "bait" protein is fused to the DNA-binding domain of a transcription factor, and the expressed sequence library is fused to the transactivation domain of the same transcription factor. Both fusion proteins are expressed in yeast cells in which the expression of a responder gene is dependent on assembly of the transcription factor on upstream DNA, which is in turn dependent on an interaction between the bait protein and a product of the expressed sequence library. Thus, interactors are identified by responder signal generation. This method suffers from a number of limitations, including high false positive and false negative rates due to (1) the inherent variability of a multi-step signal generator, (2) variability due to the broad distribution of stabilities of expressed sequences fused to a meta-stable protein fragment, and (3) the need for heterologous proteins to translocate into and be stable in the alien environment of the yeast cell nucleus.

The current invention circumvents most of the aforesaid limitations of the yeast two-hybrid system to greatly improve the efficiency of identification of natural protein-protein interactions in expressed sequence libraries. In particular, the invention allows signal generation directly from target interactions without intervening inter-molecular steps, the components of the invention are stable and therefore likely to have a stabilizing effect on unstable expressed sequence products, and finally the invention can be deployed in the natural environments of the target interactions.

Figure 5:
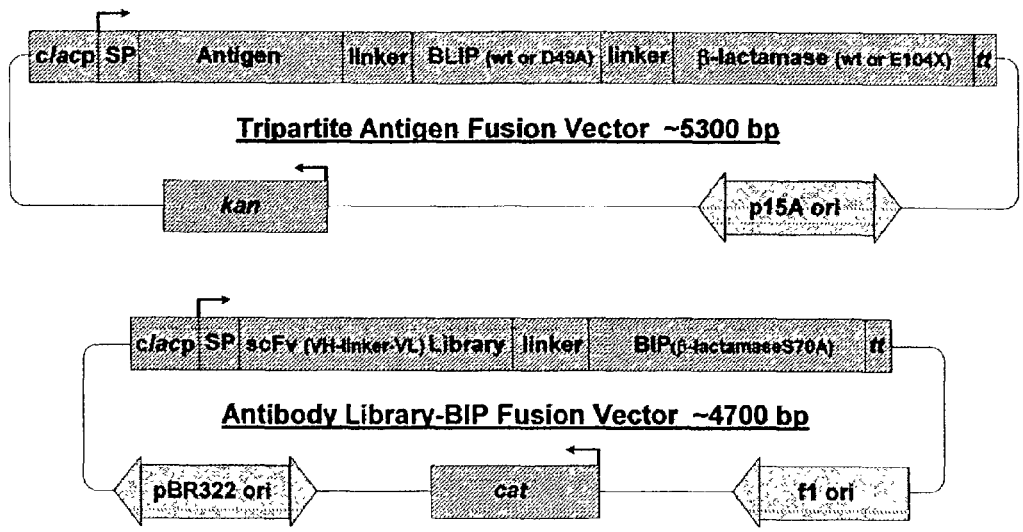
FIG. 5 shows exemplary vectors for the expression in the *E. coli* periplasmic space of components for isotropic binding molecule selection of antibodies against all available epitopes on an antigen of interest using a β-lactamase reactivation system of the present invention. In the first step, the antigen, linked to the amino terminus of the BLIP-β-lactamase fusion, is co-expressed in *E. coli* cells with a library of antibody scFv fragments linked to the amino terminus of the reactivator, in this case BIP. The cells are then selected for growth in the presence of antibiotic. Only cells in which the scFv is able to bind to the antigen, thereby facilitating the reactivation of β-lactamase, will be able to grow in the presence of the antibiotic. In the second step, selected scFv are sub-cloned for expression as fusions to the amino terminus of the BLIP-β-lactamase fusion, and co-expressed with the free antigen and the scFv library-reactivator fusion. The cells are again selected for growth in the presence of antibiotic, such that surviving colonies will be expressing pairs of complementing scFv, which can activate β-lactamase only when bound simultaneously to the free antigen. lacp, inducible lacUV5 promoter; clacp, constitutive mutant of the lacUV5 promoter; SP, signal peptide for translocation to the periplasmic space; tt, transcription terminator; kan, kanamycin resistance gene; cat, chloramphenicol resistance gene; p15A ori and pBR322 ori, compatible plasmid origins of replication; fl ori, filamentous phage origin of replication
Figure 5:
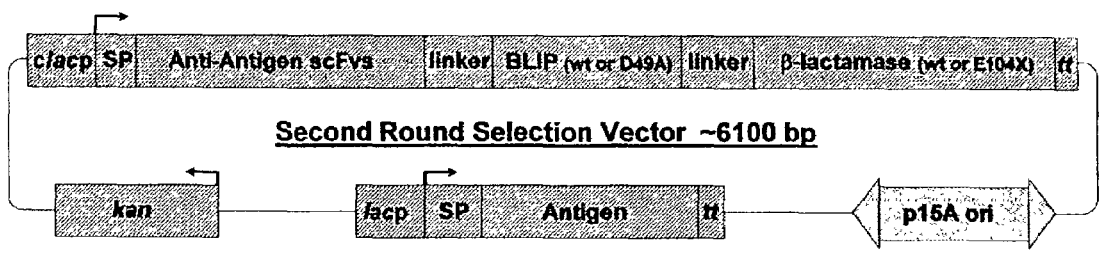
Figure 6:
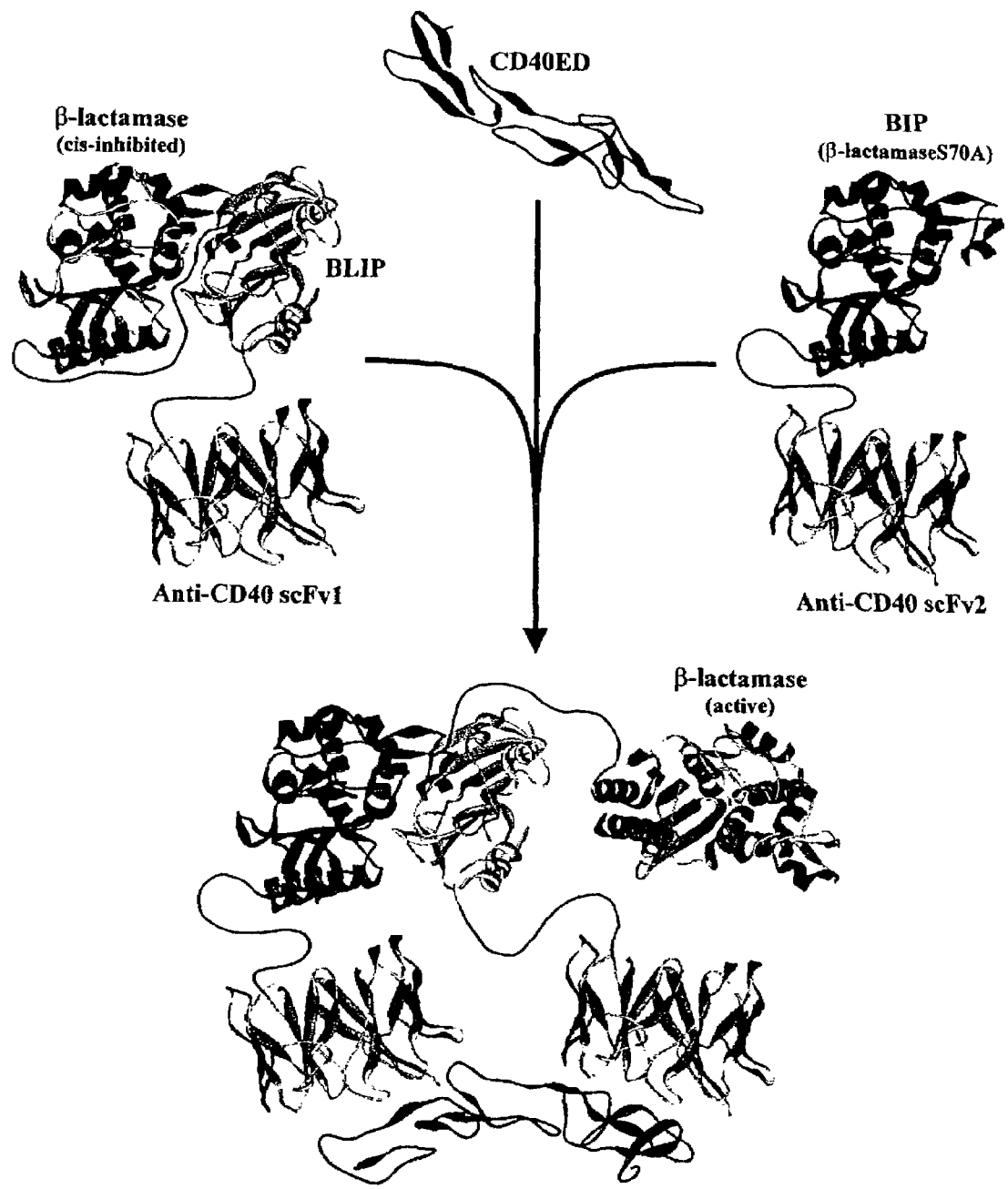
FIG. 6 shows a structural model of the reactivation of BLIP-inhibited β-lactamase by simultaneous binding of two antibody scFv fragments to non-overlapping epitopes on a free model antigen, in this case, the extra-cellular domain of the human B-cell activation antigen, CD40. The BLIP and β-lactamase structures were rendered from the x-ray crystal coordinates of Lim et al., 2001 (*Nat. Struct. Biol.* 8: 848ff). The scFv structures were rendered from the x-ray crystal coordinates of a model scFv (Eigenbrot et al., (1993) *J. Mol. Biol.* 229: 969ff). The CD40 structure was rendered from the NMR-derived solution coordinates of Bajorath and Aruffo, 1997 (*Proteins: Struct, Funct., Genet.* 27: 59-70).
Figure 9:
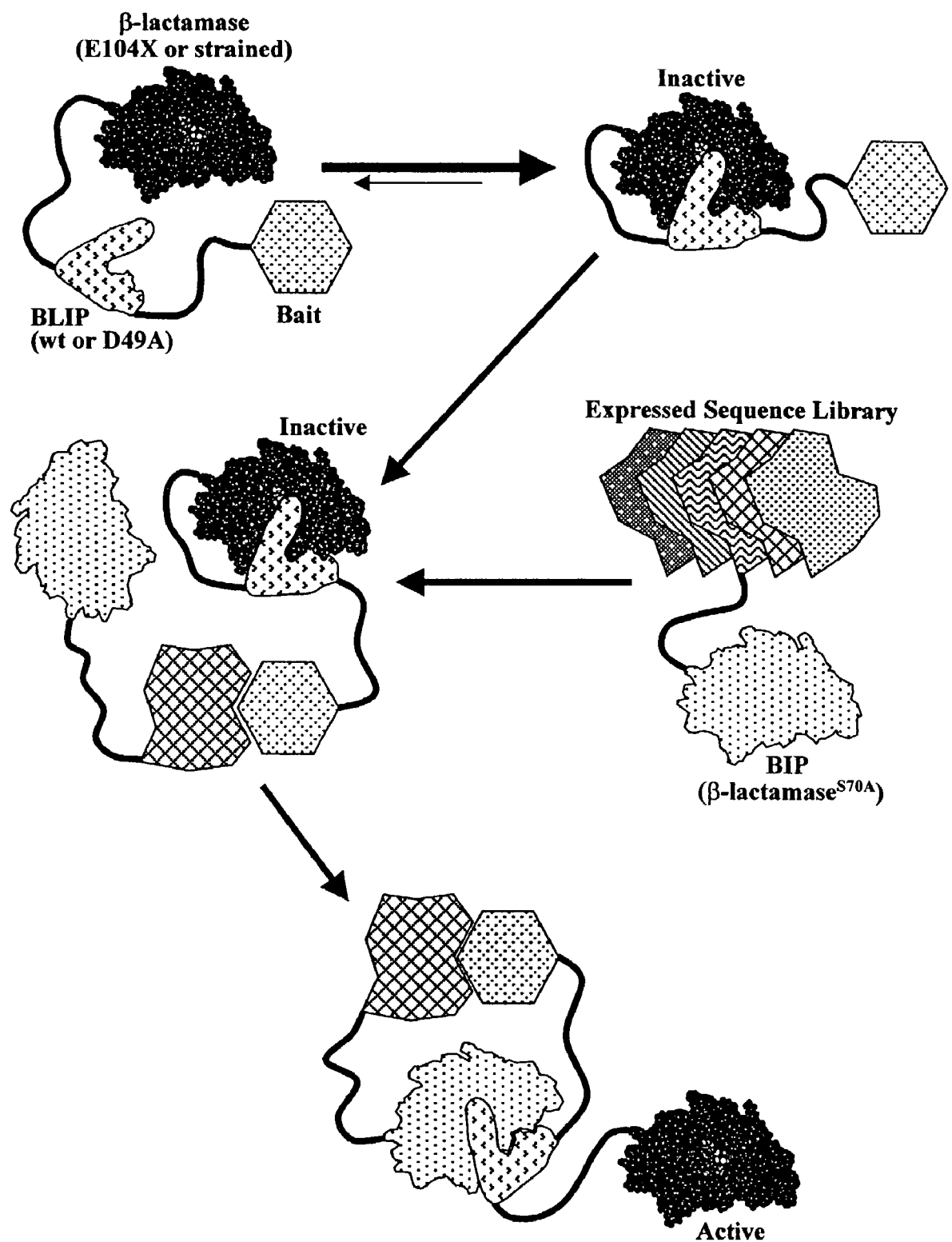
FIG. 9 depicts selection of natural interactors from an expressed sequence library with a bait protein of interest using a β-lactamase reactivation system of the present invention. The bait protein is depicted as linked to the amino terminus of the BLIP-β-lactamase fusion, and the expressed sequence library is linked to the amino terminus of the reactivator, in this case BIP. Only cells expressing natural ligands of the bait protein will be able to reactivate β-lactamase and grow in the presence of the antibiotic.

In one embodiment of the invention, illustrated in FIG. 9, the bait protein is expressed as a fusion to the amino terminus of an inhibitor-responder fusion, e.g., BLIP-β-lactamase, and the expressed sequence library is expressed as a fusion to the amino terminus of a reactivator of the responder, which in the case of β-lactamase would be BIP. The β-lactamase-BLIP affinity is reduced by virtue of a D49A mutation in BLIP, and/or by an E104K, D, Q, or A mutation in β-lactamase, and/or by linker-induced strain, so that the enzyme is fully inhibited in cis, but can be readily reactivated when docked to BIP by an interaction of the bait protein with an expressed sequence product. This system can be expressed in a variety of cell types, including prokaryotic and eukaryotic cells. For expression in bacterial cells, vectors analogous to those depicted in FIG. 5A can be used, except that the "antigen" would be replaced by the "bait" and the antibody scFv library would be replaced by an expressed sequence library. These vectors may be introduced into *E. coli* cells efficiently, for example, by chemical transformation or by high-voltage electroporation (Sambrook and Russell, supra).

When deployed in the bacterial periplasmic space, such a system would be especially well suited for identifying interactions among secreted proteins such as receptors and biological response modifiers. This is accomplished by transforming the cells with both vectors such that each cell expresses one member of the expressed sequence library along with the bait protein fusion. The cells are then plated on solid medium containing a β-lactam antibiotic such as ampicillin at a concentration which is lethal for cells in which an interaction with the bait protein does not occur, so that only cells expressing an expressed sequence product which interacts with the bait will form colonies. DNA libraries can be enriched for secreted protein sequences by templating from microsomal mRNAs. The isolation of rough microsomes and the preparation of mRNA therefrom (Gaetani et al, (1983) *Methods in Enzymology* 96, 3-24; Natzle et al. (1986) *J. Biol. Chem.* 261, 5575-5583), as well as the construction from such mRNAs of cDNA libraries suitable for use in the present invention may be accomplished using standard art (see, e.g., Sambrook and Russell, supra; and Current Protocols in Molecular Biology, supra).

Systems of the invention can also be deployed in the cytoplasmic compartment of cells, and this embodiment would be especially well-suited for identification of interactions which occur naturally in that compartment, such as those of the signal transduction pathways. For expression of the β-lactamase system in the *E. coli* cytoplasm, the same vectors as described above may be used with the coding sequences for the signal peptides removed. Since antibiotic resistance cannot be used for selection when β-lactamase is activated in the cytoplasm, color screening or selection must be employed, using a chromogenic or fluorogenic substrate. For example, the fluorogenic substrate CCF2/AM (see, e.g., Zlokamik et al., (1998) *Science* 279: 84-88) may be used, and expressed sequence products which interact with the bait protein may be recovered by subjecting the cells to fluorescence activated cell sorting (FACS, Wehrman et al., (2002) *Proc Natl Acad Sci*, in press).

Vectors for expressing the components of the system in eukaryotic cells such as yeast or mammalian cells are also known in the art (see, e.g., Sambrook and Russell, supra; and Current Protocols in Molecular Biology, supra), and β-lactamase is known to be stable and active in the mammalian cell cytoplasm (e.g., Moore et al. (1997) *Analytical Biochem.* 247: 203-209; Wehrman et al., supra). Vectors constructed to express the bait-BLIP-β-lactamase tri-partite fusion and the BIP-expressed sequence library fusions can be transfected into mammalian cell lines such as NIH 3T3 or Cos-7 cells with high efficiency by calcium phosphate co-precipitation or lipofection. Transformed cells will express the system components transiently at high levels, typically for up to 3 days, during which time the cells may be pulsed with fluorogenic substrate and subjected to FACS to enrich for cells expressing bait protein interactors. Stable transformants of the FACS-selected cells may be made by antibiotic selection, after which the putative bait protein interactors may be sequenced, identified, and subjected to verification tests such as co-immunoprecipitation with the bait protein.

Signal Transduction Pathway Sensors

Many steps in the signal transduction pathways by which cell growth and differentiation are regulated in response to environmental factors are activated post-translationally, e.g., by phosphorylation of one interactor, which then enables its recognition by another interactor. Systems of the present invention can be used to monitor the activation of key signal transduction pathways by entraining the components of responder activation to phosphorylation-dependent interactions. For example, a number of components in the EGFR/MAPK growth signaling pathways have been found to be over-expressed or mutated to constitutive activity in cancer cells (e.g., Seger and Krebs (1995) *FASEB J.* 9: 726-735). A general feature of such conditions is amplification of the MAPK pathway into a self-generating mitogenic signaling cycle in which the loop is closed by MAPK-induced autocrine growth factor production. One of the more common oncogenes is ErbB2, which is often over-expressed in adenocarcinomas of epithelial origin in breast, ovary, intestine, lung, and other tissues. ErbB2 is the most active of the EGFRs, and generally functions as a signal amplifier in hetero-dimers with other ligated receptors.

A key player in signal transmission from activated ErbB2 to the MAPK pathway is growth factor receptor binding protein 2 (Grb2) which contains a src-homology phosphotyrosine binding domain (SH2) flanked by two polyproline-binding domains (SH3). The SH2 domain binds phosphotyrosine 1068 of the receptor C-terminal domain, and the SH3 domains bind SOS, a guanine nucleotide exchange factor, thereby docking SOS to the plasma membrane where it can activate Ras, a small GTPase, which in turn activates Raf-1, the first kinase in the MAPK pathway. Thus, a number of key interactions in this pathway, including that of the Grb2 SH2 domain with phosphotyrosine 1068 of the ErbB2 C-terminal domain may be coupled with the interaction-dependent β-lactamase reactivation components of the present invention to provide facile biosensors for monitoring the activation of this pathway in relevant human cells.

For example, Grb2 may be fused via flexible linker to the amino terminus of the BLIP-β-lactamase fusion, and BIP or BLIP-F142A may be similarly fused to the carboxyl terminus of ErbB2. A vector expressing these constructs may then be introduced, e.g., by lipofection, into an appropriate cancer cell line, such as the SK-BR3 human breast tumor line, in which autocrine signaling through the ErbB2 pathway is constitutive, and essential for tumor growth and survival. Since the pathway is constitutively active, Tyr1068 should be constitutively phosphorylated, and the interaction between the Grb2 SH2 domain and pTyr1068 therefore provides a pool of constitutively active β-lactamase, which can be readily detected using a fluorogenic substrate such as CCF2/AM. Antagonists of the pathway would have promising anti-cancer chemotherapeutic activities, and may be readily identified by their ability to extinguish fluorescence in these cells. Thus, these cells can be used in high-throughput screens for such antagonists.

Selection of Inhibitor

The systems of the invention can also be used to obtain molecules that inhibit the interaction between the binding ensemble members. In one embodiment, the molecules disrupt the interaction of the binding ensemble members from the responder and reactivator complexes resulting in a loss of signal from the responder. U.S. Pat. No. 6,294,330 discloses inhibitor selection/screens for a fragment based complementation systems that are adaptable to the systems of the invention. This patent is hereby incorporated by reference.

The invention will be further understood by the following non-limiting examples.

EXAMPLES

Example 1

Interaction-Mediated Reactivation of Cis-Inhibited β-Lactamase

This example demonstrates the basic functionality of the methods and systems of the invention for detecting molecular interactions and inhibitors thereof.

Figure 10:
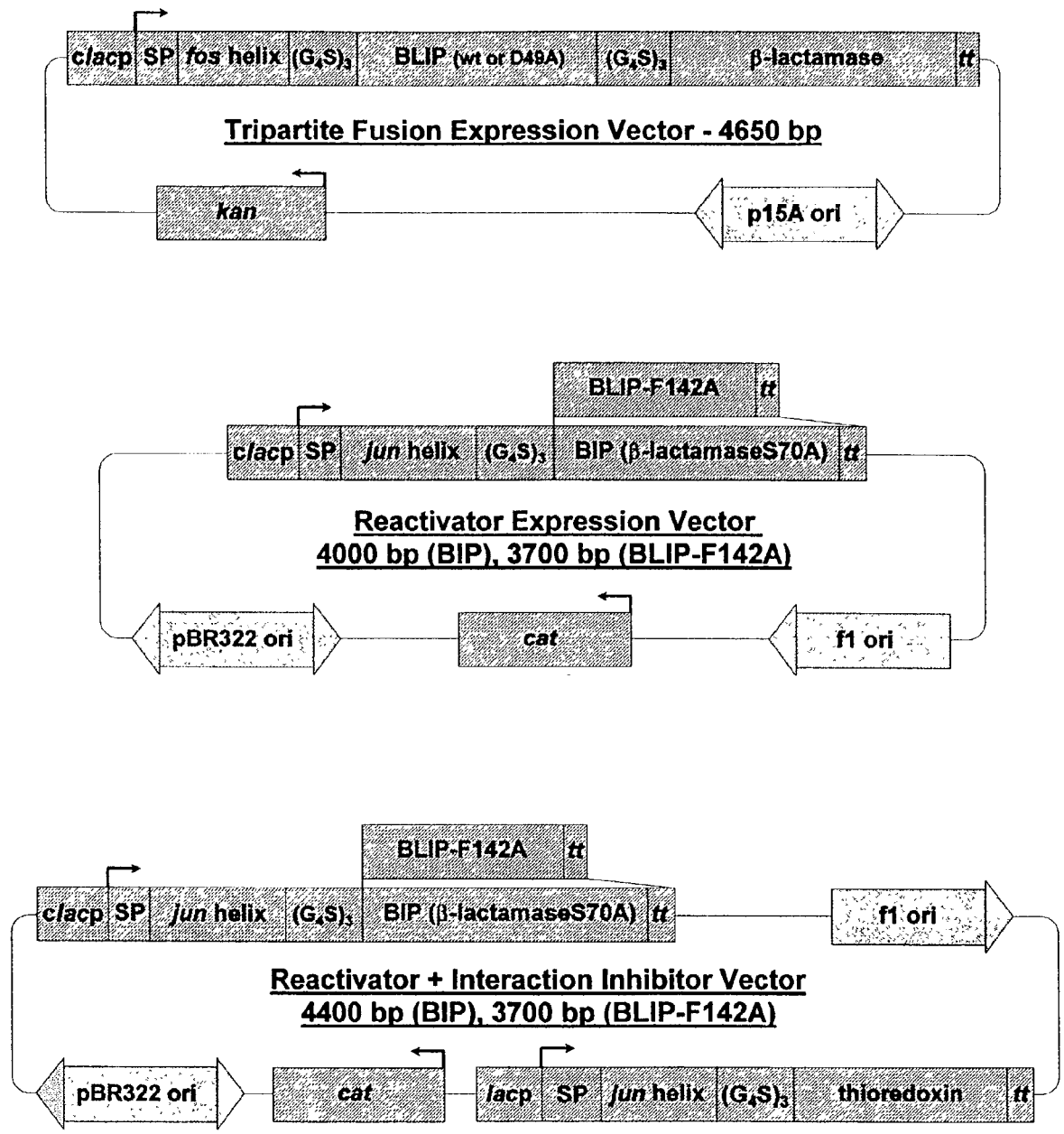
FIG. 10 shows exemplary vectors for reactivation of cis-inhibited β-lactamase by the interaction of two leucine zipper helixes from the c-fos and c-jun subunits of the AP-1 transcription factor, and for inhibition of reactivation by competitive inhibition of the helix interaction by an additional copy of the c-jun helix. The c-fos helix is fused to the amino terminus of the BLIP-β-lactamase fusion and the c-jun helix is fused to the amino terminus of the reactivator, either BIP or BLIP-F142A. For the interaction inhibitor, a second copy of the c-jun helix is expressed from the reactivator fusion vector as a fusion to the amino terminus of thioredoxin (for stability). The jun-trx fusion competes with the jun-reactivator fusion for binding to fos, thereby competitively inhibiting the reactivation of β-lactamase. Abbreviations are defined in the description of FIG. 5.

A model interaction was used to test the ability of reactivators, BIP (β-lactamase-S70A) and BLIP-F142A, to reactivate a β-lactamase responder which was strongly inhibited in cis by fusion to BLIP-D49A, when the reactivator and the cis-inhibited β-lactamase were brought together by the model interaction in *E. coli* cells. Further, the system was tested for competitive inhibition of the reactivation when the reactivating interaction was inhibited by one of the model interactors expressed from a second gene without a fusion partner. The model interaction was comprised of the leucine zipper helices of the c-fos and c-jun subunits of the AP-1 transcription factor (Karin et al., (1997) *Curr Opin Cell Biol* 9, 240-6). The c-fos helix was fused via a flexible linker to the amino terminus of the cis-inhibited responder, comprised of BLIP-D49A fused via similar linker to the amino terminus of β-lactamase. The c-jun helix was fused via a flexible linker to the amino terminus of the reactivator, either BIP or BLIP-F142A. The reactivation inhibitor was comprised of the c-jun helix fused to a chaperone, thioredoxin. The expression vectors for the tri-partite fusion, the reactivator fusion, and the reactivation inhibitor fusion are illustrated in FIG. 10.

The tri-partite fusion expression cassette was comprised of a constitutive mutant of the lacUV5 promoter, followed by the coding sequence for the tri-partite fusion protein and a transcription termination sequence. The tri-partite fusion gene comprised coding sequences for a signal peptide for translocation of the fusion protein into the periplasmic space of the bacterial cell, followed by the c-fos helix fused via a $(Gly_4Ser)_3$ linker to BLIP-D49A, followed via a similar linker by β-lactamase. This cassette was assembled in a plasmid based on the p15A replicon (Rose, *Nucleic Acids Res.* (1988) 16:355-356) containing a kanamycin resistance gene (kan) for plasmid maintenance.

The reactivator fusion expression cassette was comprised of the lacUV5 promoter, followed by the coding sequence for a signal peptide, followed by the c-jun helix fused to BIP or BLIP-F142A via a (Gly$_4$Ser)$_3$ linker. This cassette was assembled in plasmid pBR322 in which the β-lactamase gene was replaced with the gene for chloramphenicol resistance (cam) for plasmid maintenance. Negative control cassettes comprised of the reactivators without amino-terminal c-jun helices were constructed similarly. For reactivation inhibition tests, an interaction inhibitor expression cassette was inserted into the reactivator fusion vector, as illustrated in FIG. 10. This cassette was comprised of a lacUV5 promoter, and the coding sequences for a signal peptide, followed by the c-jun helix fused to thioredoxin via a (Gly$_4$Ser)$_3$ linker. All expression vectors were assembled using standard recombinant DNA methods (e.g., Sambrook and Russell, eds, *Molecular Cloning: A Laboratory Manual*, 3rd Ed, vols. 1-3, Cold Spring Harbor Laboratory Press, 2001; and *Current Protocols in Molecular Biology*, Ausubel, ed. John Wiley & Sons, Inc. N.Y., 1997). While the tripartite cis-inhibited β-lactamase fusion was constitutively expressed, expression of the reactivator fusions and the reactivation inhibitor fusions required IPTG, an inducer of the lacUV5 promoter.

*E. coli* cells (e.g., TOP10F') were transformed with these vectors by high-voltage electroporation (Dower et al. (1988) *Nucleic Acids Res.* 16: 6127-6144), and the transformed cells were plated on solid rich medium (2xYT) containing various constituents for plasmid maintenance (kanamycin, chloramphenicol, and tetracycline), regulation of the heterologous genes (glucose and IPTG), and to test for antibiotic resistance (ampicillin; for methods, see, e.g., Sambrook and Russell, eds, *Molecular Cloning: A Laboratory Manual*, 3rd Ed, vols. 1-3, Cold Spring Harbor Laboratory Press, 2001). Data reflecting growth of the transformed cells under various conditions are shown in Table I.

TABLE I

Interaction-mediated Reactivation of Cis-inhibited β-lactamase and Inhibition of Reactivation by Competitive Inhibition of the Interaction.[a.]

| Reactivator | Inhibitor | IPTG | Ampicillin (μg/ml) | | | |
|---|---|---|---|---|---|---|
| | | | 10 | 25 | 50 | 100 |
| BIP | — | — | 1% | <0.01% | <0.01% | <0.01% |
| c-jun-BIP | — | — | 3% | <0.01% | <0.01% | <0.01% |
| BLIP$^{F142A}$ | — | — | 1% | <0.01% | <0.01% | <0.01% |
| c-jun-BLIP$^{F142A}$ | — | — | 5% | <0.01% | <0.01% | <0.01% |
| BIP | — | 100 μM | 100% | 0.7% | <0.01% | <0.01% |
| c-jun-BIP | — | 100 μM | 100% | 100% | 100% | 100% |
| c-jun-BIP | c-jun-trx | 100 μM | 100% | 100% | 9% | 0.08% |
| BLIP$^{F142A}$ | — | 100 μM | 100% | 4% | <0.01% | <0.01% |
| c-jun-BLIP$^{F142A}$ | — | 100 μM | 100% | 100% | 100% | 100% |
| c-jun-BLIP$^{F142A}$ | c-jun-trx | 100 μM | 100% | 100% | 75% | 0.5% |

*E. coli* cells were transformed with the constructs of FIG. 10 to express the c-fos leucine zipper helix fused to the BLIP$^{D49A}$ - lactamase fusion BIP or BLIP$^{F142A}$ with or without the amino terminal c-jun helix, and, where indicated, further expressing the c-jun helix fused to thioredoxin (trx) as a competitive inhibitor of the reactivating fos-jun helix interaction. The transformed cells were plated on solid medium containing 2%glucose, increasing amounts of ampicillin, and, where indicated, IPTG, which is required for expression of the reactivator fusions and the interaction inhibitor. The data are expressed as % plating efficiency, i.e., the percent of transformed cells plated forming colonies after overnight growth at 33° C.

When cells expressing the cis-inhibited α-lactamase fusion and any of the reactivator constructs were plated on increasing concentrations of ampicillin in the absence of IPTG, so that only the cis-inhibited β-lactamase fusion was expressed, the cells plated with low efficiency on 10 μg/ml ampicillin and produced no colonies from at least 10,000 cells plated on higher ampicillin concentrations. In the presence of IPTG, however, when the reactivators were expressed, the β-lactamase was to varying degrees reactivated. Free BIP produced little reactivation by itself, but when fused to the c-jun helix, so that BIP could be docked to the cis-inhibited α-lactamase by the fos-jun helix interaction, β-lactamase was fully reactivated, i.e., every plated cell produced a colony on each concentration of ampicillin up to 100 μg/ml.

At 100 μg/ml ampicillin, $10^6$ cells had to be plated in a separate experiment before any colonies appeared. This suggests that bona-fide interactors, such as antigen-specific antibodies or natural ligands, can be selected for a protein of interest from a library of at least $10^5$ non-interactors in a single plating. Even lower frequency interactors can readily be isolated by replating the colonies one or more times at only a few cells per colony, so that low-efficiency platers would be partitioned out. This demonstrates the utility of the system for sensitive detection of specific protein-protein interactions.

When a competitive inhibitor of the fos-jun helix interaction was expressed in the same cells, i.e., a second copy of the c-jun helix fused to thioredoxin as a carrier, reactivation was substantially reduced, so that the plating efficiency was reduced by more than 1000-fold on 100 μg/ml ampicillin. This indicates that the system can also be used to screen efficiently for inhibitors of target interactions. The results were comparable for the BLIP-F142A reactivator, except that BLIP-F142A reactivation was more resistant to inhibition by the interaction inhibitor. This may be due to the fact that, like wild-type BLIP, BLIP-F142A stabilizes β-lactamase somewhat, so that the activity produced upon reactivation by BLIP-F142A is actually greater than that produced by BIP, since the latter would not be expected to stabilize β-lactamase. Nevertheless, these data indicate the power and efficiency of the system for detecting and selecting bona-fide protein-protein interactions.

Example 2

Antigen-Antibody Interaction-Mediated Reactivation of Cis-Inhibited β-Lactamase

This example demonstrates the utility of the invention for detection of antigen-antibody interactions, selection of antibodies against specific antigens, and affinity maturation of antibodies. Also, the ability of the system to detect free antigen molecules via a tri-molecular interaction is demonstrated. Finally, reactivation of β-lactamase by antigen-antibody interaction when the responder complex comprises non-covalent linkages is demonstrated.

The antibody used in this example was a mouse monoclonal raised against the extra-cellular domain of the human B-cell activation antigen CD40, and isolated by hybridoma technology. This antibody, designated HB15, had a $K_d$ for CD40 of 7.6 nM, as determined by surface plasmon resonance (Fägerstam et al., (1992) *J Chromatog* 597: 397-410). A higher-affinity variant of this antibody was subsequently identified which contained two mutations in the third complementarity-determining region (CDR3) of the heavy chain variable region (VH), which conferred a 12-fold increase in the affinity of the antibody. This variant was designated HB15Y.

Figure 11:
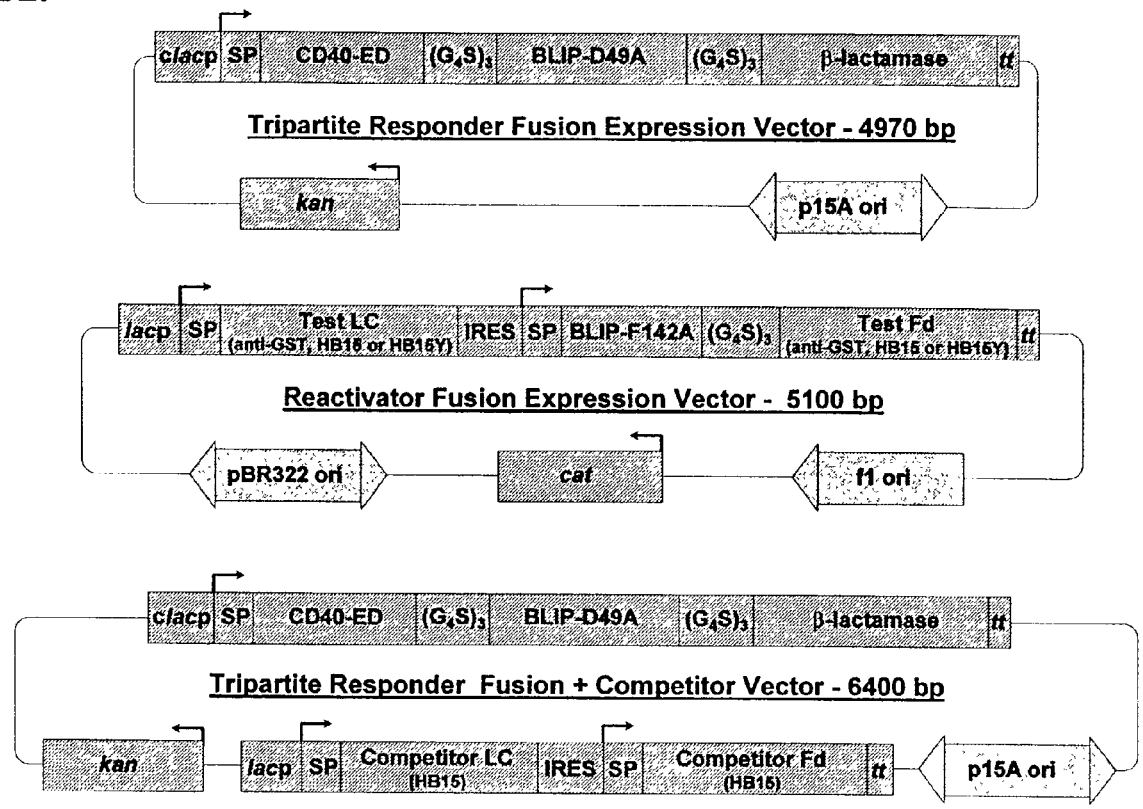
FIG. 11. A. Vectors for testing anti-CD40 antibody Fab fragments for their ability to mediate the reactivation of cis-inhibited β-lactamase when the latter is fused to CD40. The CD40 extra-cellular domain (CD40-ED) is expressed as an amino-terminal fusion to the BLIP-β-lactamase fusion, and co-expressed with three different Fabs fused to the BLIP-F142A reactivator, an anti-CD40 Fab (HB15), a higher-affinity variant of HB15 (HB15Y), and a negative control (anti-GST Fab). Each Fab was expressed from a dicistronic transcript with the light chain (LC) encoded by the upstream cistron and the Fd fragment encoded by the downstream cistron. The BLIP-F142A reactivator was fused to the amino terminus of the Fd fragment. Cells expressing the antigen fusion and each of the Fab fusions were scored for plating efficiency on increasing concentrations of antibiotic. The HB15 Fab gene was also inserted into the antigen-responder fusion vector to provide a non-activating competitor for binding to the antigen, and each Fab was tested for its ability to compete with HB15 to activate β-lactamase. IRES, internal ribosome entry site for translation of the downstream cistron. B. Vector for tri-molecular reactivation of cis-inhibited β-lactamase. The CD40-BLIP-β-lactamase fusion was split into two separate fusion proteins, each fused to an interacting leucine zipper helix and expressed from a separate gene. CD40 was fused to the amino terminus of the c-jun helix, and the c-fos helix was fused to the amino terminus of the BLIP-β-lactamase fusion. These fusions were then co-expressed with each of the anti-CD40 Fabs fused to the reactivator to test for the strength of β-lactamase reactivation when two docking interactions involving three binding ensemble members was required.
Figure 11:
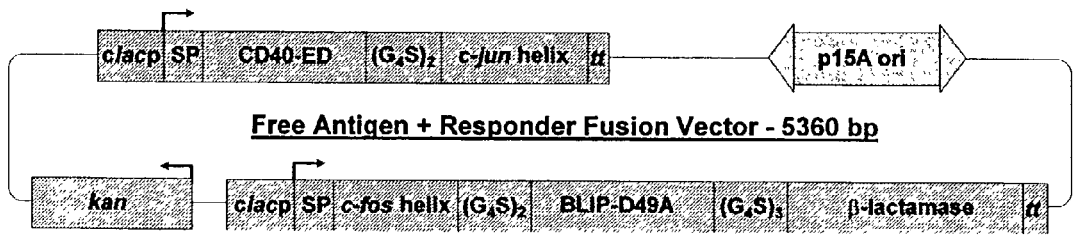
Figure 12:
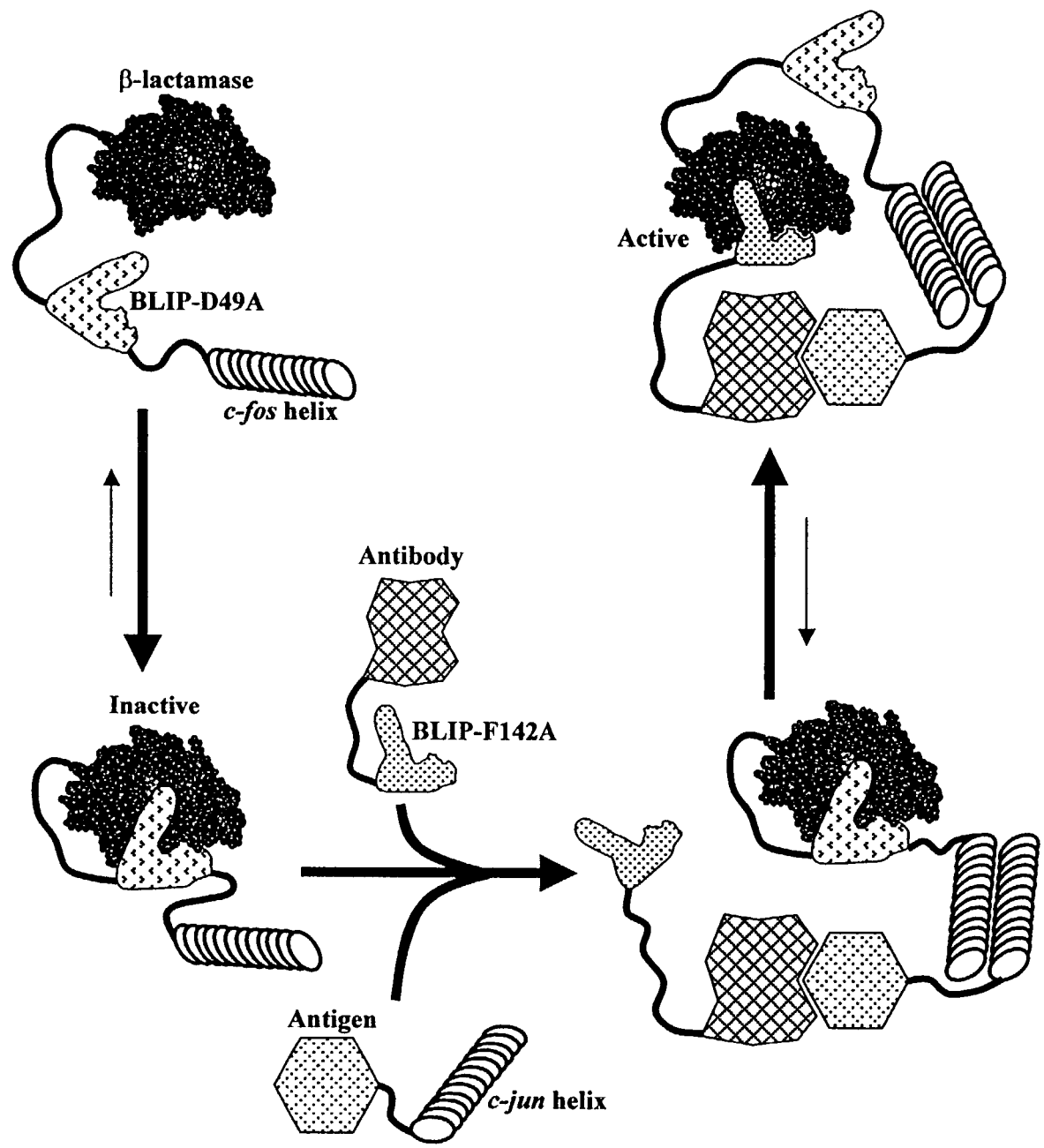
FIG. 12 provides an illustration of tri-molecular activation of cis-inhibited β-lactamase by the combined interactions of antigen with antibody and the c-fos/c-jun leucine zipper. The interaction of the c-fos and c-jun helixes docks the antigen to the BLIP-β-lactamase fusion, and the interaction of antigen and antibody docks the reactivator, in this case BLIP-F142A, to the cis-inhibited β-lactamase.

The vectors for expression of the system components for CD40-HB15 interaction-mediated reactivation of cis-inhibited β-lactamase, and for inhibition of that reactivation by a competitor antibody are depicted in FIG. 11. The CD40- in a single plating. Even lower frequency binders could readily be isolated by replating the colonies one or more times at only a few cells per colony, so that low-efficiency platers would be partitioned out. This demonstrates the utility of the system for sensitive detection of antigen-antibody interactions, and for selection of even rare high-affinity antigen-specific antibodies.

TABLE II

Reactivation of Cis-inhibited β-lactamase by Antigen-Antibody Interaction and Competitive Reactivation based on Affinity[a.]

| Test Fab | Test Fab $K_d$ | Competitor | Ampicillin (μg/ml) | | | | |
|---|---|---|---|---|---|---|---|
| | | | 10 | 25 | 50 | 100 | 200 |
| Anti-GST | ∞ | — | 15% | <0.01% | <0.01% | <0.01% | <0.01% |
| HB15 | 7.6 nM | — | 100% | 100% | 100% | 100% | 100% |
| HB15Y | 0.6 nM | — | 100% | 100% | 100% | 100% | 100% |
| HB15 | 7.6 nM | HB15 | 100% | 100% | 25% | 0.2% | 0.04% |
| HB15Y | 0.6 nM | HB15 | 100% | 100% | 80% | 100% | 2% |

[a.]*E. coli* cells were transformed with the constructs of FIG. 11 to express CD40 fused to cis-inhibited β-lactamase, the indicated test Fabs fused to BLIP-F142A as the reactivator, and, where indicated, HB15 as the competitor. Transformed cells were plated on solid medium containing 2% glucose, 100 μM IPTG, and the indicated concentrations of ampicillin. The data are expressed as plating efficiencies, i.e., the percent of transformed cells plated which formed colonies after overnight growth at 33° C.

BLIP-D49A-β-lactamase fusion contained (Gly$_4$Ser)$_3$ linkers and was expressed from a constitutive mutant of the lacUV5 promoter in a p15A plasmid containing a kanamycin resistance gene (kan) for plasmid maintenance. The HB15 antibodies were expressed in chimeric Fab form, i.e., VH-CH1 (Fd) with full-length light chain (LC), in which both constant regions were human in origin. The Fabs were expressed from dicistronic transcripts driven by the lacUV5 promoter. The upstream cistron encoded the LC, followed by an internal ribosome entry site (IRES) to allow translation to re-initiate on the downstream cistron, which encoded BLIP-F142A fused (Gly$_4$Ser)$_3$ linker to the amino terminus of the Fd fragment of either HB15 or HB15Y. This reactivator/Fab fusion cassette was inserted into plasmid pBR322 in which the β-lactamase gene had been replaced by the gene for chloramphenicol resistance (cat) for plasmid maintenance. To demonstrate the ability of the system to detect higher-affinity variants of an antibody, the reference antibody, HB15 Fab, was expressed as a free competitor from a separate cassette inserted into the tri-partite CD40-BLIP-β-lactamase vector. Finally, a Fab specific for an irrelevant antigen, glutathione S-transferase (GST), was used as a negative control.

Table II presents data showing the ability of the interaction between CD40 and anti-CD40 Fabs to facilitate strong reactivation of the cis-inhibited β-lactamase/BLIP-D49A fusion by the BLIP-F142A reactivator when antigen and antibody are fused to the inhibited responder and reactivator, respectively. Whereas, host cells expressing the anti-GST Fab as the test Fab fused to the reactivator produced less than one colony per 10,000 cells plated on 25 μg/ml ampicillin and above, both the HB15 and HB15Y Fabs plated at 100% efficiency up to at least 200 μg/ml ampicillin. In a separate experiment up to a million cells expressing the anti-anti-GST Fab were plated and still no colonies appeared, though when co-expressed with GST fused to cis-inhibited β-lactamase this antibody could reactivate β-lactamase just as well as the CD40-anti-CD40 interaction. This suggests that antigen-specific antibodies can be selected from a library of at least 10$^6$ non-binding antibodies When the same HB15 antibody was expressed without a fusion partner in the same cells, i.e., as a competitive inhibitor of the reactivating CD40-HB15 interaction, the plating efficiency was reduced by 500-fold on 100 μg/ml ampicillin, and by 2500-fold on 200 μg/ml. However, when the same competitor was co-expressed with HB15Y, the higher-affinity variant, the plating efficiency was increased by 500-fold on 100 μg/ml ampicillin relative to the parent antibody. The system apparently could not discriminate between HB15 and the 12-fold higher-affinity variant in the absence of a competitor, presumably because the working concentrations in the cells were higher than the $K_d$s, so antibody affinity was not limiting for β-lactamase activity. However, in the presence of the competitor the higher-affinity variant could readily be distinguished from the parent. With a 500-fold higher plating efficiency, this variant may be isolated from a background of 10$^6$ unimproved variants by re-plating three times at no more than ten cells per colony on 100 μg/ml ampicillin. This demonstrates the utility of the invention for antibody affinity maturation.

a. Antigen-Antibody Interaction-Mediated Reactivation of Cis-Inhibited β-Lactamase Using a Tri-Molecular System in Which a Binding Ensemble Member is Non-Covalently Linked to the Responder Complex.

The CD40-anti-CD40 interaction was further used to test the invention for its ability to detect a free binding ensemble member in a tri-molecular interaction. In this embodiment of the invention one binding ensemble member (CD40 antigen) is linked non-covalently in the responder complex. Instead of being fused directly to the amino terminus of the inhibitor, BLIP-D49A, in the cis-inhibited β-lactamase complex, CD40 was instead fused to the c-jun leucine zipper helix, and the c-fos helix was fused to the amino terminus of the BLIP-D49A-β-lactamase fusion. In this configuration the high affinity fos-jun helix interaction links the antigen non-covalently to the cis-inhibited responder complex, so that antibody binding to the antigen can dock the reactivator to the responder. This and similar configurations have the advantage that binding ensemble members which do not tolerate fusion partners such as the components of the system, will nevertheless usually tolerate the addition of much smaller fusion partners such as high-affinity leucine zipper helixes, which can then be used to non-covalently dock the binding ensemble members to the components of the system. The fos and jun fusions were each expressed from constitutive lacUV5 promoters in separate cassettes in the cis-inhibited responder vector. Again, the anti-GST Fab served as the negative control, fused to the reactivator.

The fos and jun fusions were co-expressed in *E. coli* cells with each of the Fabs, anti-GST, HB15, and HB15Y fused to the BLIP-F142A reactivator, and scored for plating efficiency on increasing amounts of ampicillin. The plating efficiency data are shown in Table III. As expected, with the anti-GST Fab, no colonies appeared above 10 g/ml ampicillin. However, with the HB15 and HB15Y anti-CD40 Fabs, plating was nearly as robust as when the antigen was fused directly to the cis-inhibited responder. From this, it may be concluded that non-covalent linkages can replace covalent linkages in the responder complex, and still allow responder reactivation by interaction of binding ensemble members, at least one of which is not covalently linked to either the cis-inhibited responder or the reactivator. Further, this example demonstrates by equivalence that cis-inhibited responders can be reactivated efficiently by tri-molecular interactions in which two non-competing antigen binders (antibody and helix) engage free antigen (CD40-helix fusion) to dock the reactivator to the cis-inhibited responder, activating the latter.

TABLE III

Reactivation of Cis-inhibited β-lactamase by Free Antigen in a Tri-molecular complex with Antibody and Leucine Zipper[a.]

| Test Fab | Ampicillin (μg/ml) | | | | |
|---|---|---|---|---|---|
| | 10 | 25 | 50 | 100 | 200 |
| Anti-GST | 15% | <0.01% | <0.01% | <0.01% | <0.01% |
| HB15 | 100% | 83% | 100% | 77% | 0.8% |
| HB15Y | 100% | 100% | 100% | 60% | 12% |

[a.]E. coli cells were transformed with the constructs of FIG. 11B to express CD40 fused to a c-jun helix, a c-fos helix fused to cis-inhibited β-lactamase, the indicated test Fabs fused to BLIP-F142A as the reactivator. Transformed cells were plated on solid mediumcontaining 2% glucose, 100 μM IPTG, and the indicated concentrations of ampicillin. The data are expressed as plating efficiencies, i.e., the percent of transformed cells plated which formed colonies after overnight growth at 33° C.

b. Antigen-Antibody Interaction-Mediated Activation β-Lactamase When the Responder and Inhibitor are Non-Covalently Linked in the Responder Complex.

In this variant of the system the responder and the inhibitor are non-covalently linked in the responder complex, and the binding ensemble member is covalently linked to the inhibitor. This is accomplished by expressing the CD40-BLIP fusion and β-lactamase from separate cistrons in the responder expression vector. To ensure constitutive inhibition of β-lactamase, wild-type BLIP may be used instead of the D49A mutant. For this system the responder expression vector shown in FIG. 11A is modified by replacing the coding sequence for the $(G_4S)_3$ linker between BLIP and β-lactamase with a DNA sequence encoding a translation stop codon at the end of BLIP, followed by an internal ribosome entry site (IRES) for translation of β-lactamase, followed by a translation start codon and signal peptide for production and secretion of free β-lactamase. When this vector is expressed alone, β-lactamase is largely inhibited, and remains so when co-expressed with a reactivator fusion comprised of a low-affinity BIP (e.g., E104X) fused to a negative control Fab such as anti-GST. However, when co-expressed with a BIP-E104X fused to an anti-CD40 Fab, the antigen-Fab interaction docks BIP to BLIP, thereby activating α-lactamase by neutralizing BLIP The mechanism for this mode of α-lactamase activation when the responder and inhibitor are non-covalently linked is illustrated in FIG. 4.

The CD40-BLIP fusion and β-lactamase were co-expressed in *E. coli* cells with each of the Fabs, anti-GST, HB15, and HB15Y fused to the BIP-E 104Q reactivator, and scored for plating efficiency on increasing amounts of ampicillin. The Reactivator Fusion Expression Vector is the same as shown in FIG. 11A, except that BIP-E104Q replaces BLIP-F142A as the reactivator. The plating efficiency data are shown in Table IV. As expected, with the anti-GST Fab, no colonies appeared above 10 μg/ml ampicillin. However, with the HB15 and HB15Y anti-CD40 Fabs, plating was quantitative on at least 50 μg/ml ampicillin for HB15, and on at least 100 g/ml for the higher-affinity HB15Y. These levels of activation compare favorably with reactivation when the inhibitor and responder are covalently linked. From this, it may be concluded that non-covalent linkages can replace covalent linkages in the responder complex, and still allow efficient responder activation by interaction of binding ensemble members when inhibitor and responder are not covalently linked.

TABLE IV

Activation of β-lactamase by Antigen-Antibody Interaction-mediated Sequestering of the Inhibitor BLIP[a.]

| Test Fab | Ampicillin (μg/ml) | | | | |
|---|---|---|---|---|---|
| | 10 | 25 | 50 | 100 | 200 |
| Anti-GST | 21% | <0.01% | <0.01% | <0.01% | <0.01% |
| HB15 | 100% | 100% | 100% | 12% | 0.2% |
| HB15Y | 100% | 100% | 100% | 100% | 1% |

[a.]E. coli cells were transformed with a responder complex construct expressing β-lactamase and CD40 fused to the BLIP inhibitor, and a reactivator complex construct expressing the BIP-E104Q reactivator fused to each of the indicated test Fabs. Transformedcells were plated on solid medium containing 2% glucose, 100 μM IPTG, and the indicated concentrations of ampicillin. The data are expressed as plating efficiencies, i.e., the percent of transformed cells plated which formed colonies after overnight growth at 33° C.

It should be noted that β-lactamase activation by antigen-antibody interaction with non-covalent linkage of responder and inhibitor in the responder complex could have been accomplished with equal efficiency by covalently linking the binding ensemble member (CD40) to the responder instead of to the inhibitor. In this case, BLIP-F142A would be used as the reactivator fused to the Fabs, such that a CD40-Fab interaction would dock BLIP-F142A to β-lactamase, thereby protecting it from inhibition by BLIP.

Example 3

Re-Activation of Cis-Inhibited β-Lactamase In Vitro by Antigen-Antibody Interaction.

This example demonstrates the ability of systems of the invention to function in vitro and to detect analytes of interest in biological specimens.

The system components described in Example 2, i.e., the CD40-BLIP-D49A-βlactamase fusion, and the fusions of anti-GST Fab, HB15, and HB15Y with BLIP-F142A (see FIG. 11, Tripartite Responder Fusion Expression Vector, and Reactivator Fusion Expression Vectors), were purified from suspension cultures, and then mixed in vitro with a chromogenic substrate to test for antibody-specific β-lactamase activation. Each of the fusion proteins was equipped with a carboxyl-terminal His$_6$ tag for purification by immobilized metal ion affinity chromatography (IMAC; Janknecht et al. (1991) Proc Natl Acad Sci USA 88: 8972-6). Separate one-liter cultures of each construct in *E. coli* TOP10F' cells (Invitrogen Corp., Carlsbad, Calif.) were grown to mid-log phase in 2xYT medium supplemented with antibiotics (either kanamycin or chloramphenicol) for plasmid maintenance. Expression of the fusion protein was then induced for 4 hours with 1 mM IPTG, and the cells were collected and lysed in PBS supplemented with 150 mM NaCl, 1% Triton X100, 5% Glycerol, 10 mM Benzamidine, (Sigma Chemical Co., St. Louis, Mo.) *E. coli*-specific protease inhibitor cocktail and 1 mM PMSF. The fusion proteins were batch-purified by IMAC with a kit from Amersham Pharmacia Biotech (Piscataway, N.J.). Purity, quantity, and integrity of the fusion proteins was determined by SDS-PAGE on a 4-20% gradient gel, followed by immunoblotting with an anti-His6 antibody (Amersham). All purified proteins were judged to be largely intact and at least 75% pure by this criterion. Yields ranged from 28 µg to 55 µg per liter of culture. All methods can be found in the product literature; in Sambrook and Russell, eds, Molecular Cloning: A Laboratory Manual, 3rd Ed, vols. 1-3, Cold Spring Harbor Laboratory Press, 2001; and in Current Protocols in Molecular Biology, Ausubel, ed. John Wiley & Sons, Inc. N.Y., 1997.

Figure 13:
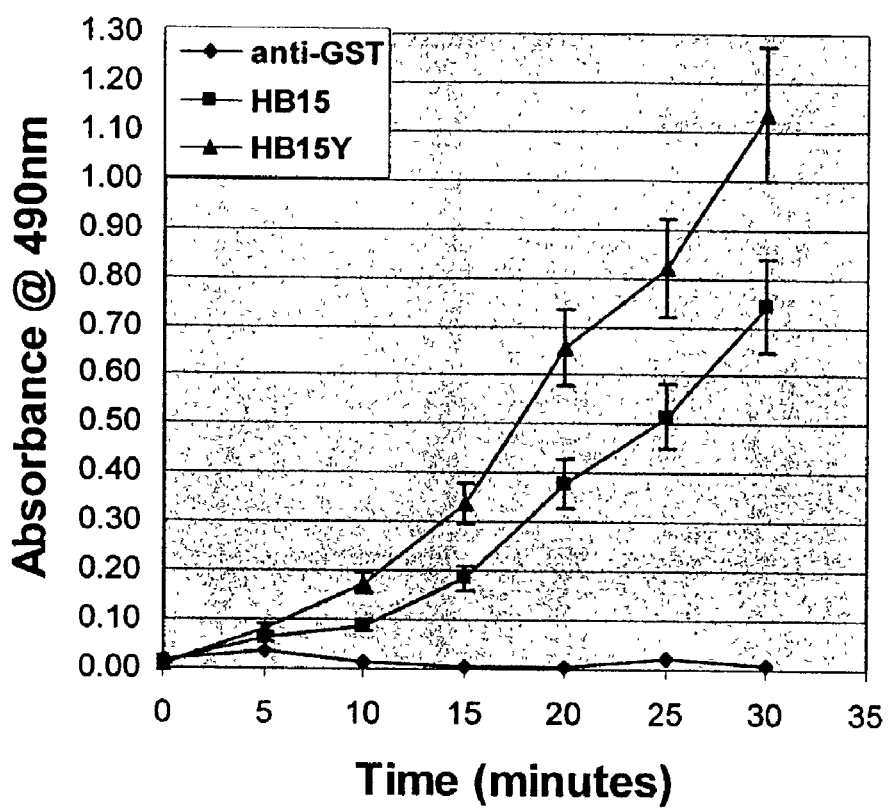
FIG. 13 shows enzymatic activities of β-lactamase reactivated in vitro by antigen-antibody interactions. A. Reactions containing approximately 0.1 µM purified CD40-BLIP-β-lactamase fusion and 0.1 µM of the indicated purified Fab/reactivator fusions in PBS were initiated with the addition of an excess (~1 mM) of the chromogenic β-lactamase substrate nitrocefin (λmax=485 nm), and were incubated for 30' at 30° C., during which the reaction progress was monitored by absorbance at 490 nm. Error bars represent the standard deviation of triplicate samples. B. To test the ability of the system to detect and quantify free analytes in biological specimens using a tri-molecular interaction, the c-fos helix fusion of BLIP-β-lactamase, depicted in FIG. 11, was also purified, and the reactions with the CD40-c-jun helix fusion and the Fab/reactivator fusions were reconstituted in vitro. Reactions containing approximately 0.5 µM each of this fusion and the Fab/reactivator fusion in clarified lysate of cells expressing the CD40-jun helix fusion were initiated with 1 mM nitrocefin, and the mixtures were incubated for 30' at 30° C., after which the reaction product was measured by absorbance at 490 nm. Error bars represent the standard deviation of triplicate samples.
Figure 13:
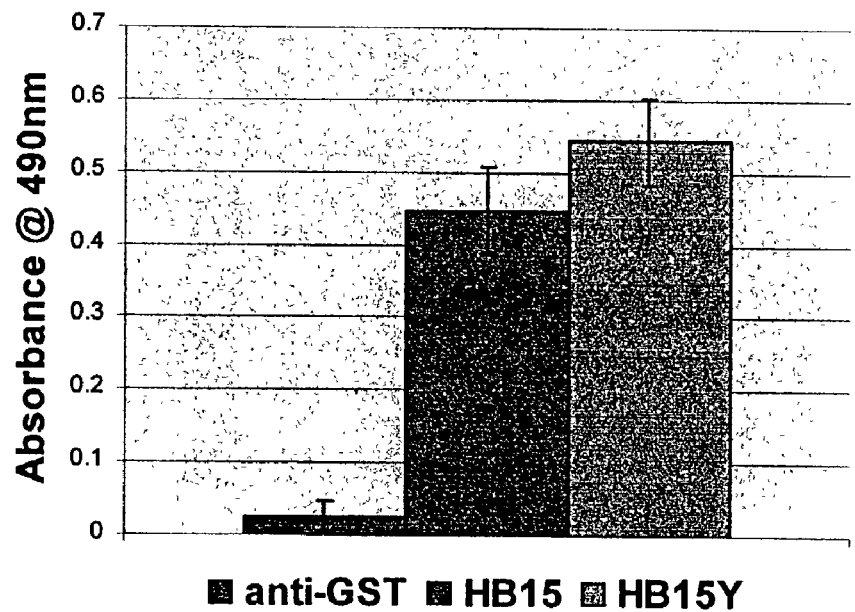

50 µl reactions containing approximately 0.1 µM CD40-BLIP—-lactamase fusion and 0.1 µM Fab/reactivator fusion in PBS with an excess (1 mM) of the chromogenic β-lactamase substrate nitrocefin (λmax=485 nm; $\epsilon$=17, 420 M$^{-1}$ cm$^{-1}$; McManus-Munoz and Crowder (1999) Biochemistry 38, 1547-53) were incubated in triplicate in microtiter plate wells for 30' at 30° C., during which the reaction progress was monitored by absorbance at 490 nm using a BioRad Benchmark Microplate Reader (Bio-Rad Corp., Richmond, Calif.). The results are shown in FIG. 13A. While the anti-GST Fab/BLIP142A reactivator fusion produced no time-dependent increase in the activity of the cis-inhibited β-lactamase, both the HB15 and HB15Y Fabs produced a steady increase in β-lactamase activity throughout the 30' incubation period. In both cases the reaction product appeared to accumulate exponentially for ~15-20 minutes before equilibrium was reached, after which the product appeared to accumulate more or less linearly. The HB15Y Fab consistently outpaced the lower affinity HB15 antibody, as might be expected from its higher affinity. Since the dissociation rates for both Fabs are expected to be low compared to the time scale of this reaction, the higher reaction rate for the HB15Y Fab specifically implies a higher association rate constant for this antibody.

To test the ability of the system to detect and quantify free analytes in biological specimens using a tri-molecular interaction, the c-fos helix fusion of BLIP-β-lactamase, depicted in FIG. 11, was also purified, and the reactions with the CD40-c-jun helix fusion and the Fab/reactivator fusions were reconstructed in vitro. Triplicate 50 µl reactions each contained approximately 0.5 µM of this fusion and 0.5 µM Fab/reactivator fusion in clarified lysate of cells expressing the CD40-jun helix fusion. To each was added an excess (1 mM) of the nitrocefin substrate and the mixtures were incubated in microtiter plate wells for 30' at 30° C., after which the reaction product was measured by absorbance at 490 nm. The results are shown in FIG. 13B. The anti-GST Fab detected no CD40 above machine background, whereas both the HB15 and HB15Y Fabs detected CD40 in amounts at least 20-fold above the background. Again, the higher signal produced by HB15Y presumably reflects the faster association rate of the higher-affinity Fab. These results demonstrate the utility of systems of the invention for rapid and sensitive detection and quantification of analytes in biological specimens in a homogeneous kinetic reaction in vitro.

Example 4

An Antibody-Antigen Interaction-Mediated β-Lactamase Reactivation System for Target-Activated Enzyme Prodrug Therapy (TAcEPT)

Antibody-directed enzyme prodrug therapy (ADEPT) is a promising anti-cancer chemotherapeutic strategy which takes advantage of the catalytic power of enzymes to amplify the cytotoxicity-targeting power of tumor-specific antibodies. Enzymes are concentrated at the tumor site when administered as conjugates of tumor-specific antibodies. After unbound conjugate has cleared from the circulation, prodrugs may be administered which are relatively non-toxic until activated by the tumor-bound enzyme, whereupon the cytotoxic product may accumulate at the tumor site to concentrations which would be unattainable by parenteral administration of the drug without excessive toxicity. Enzymes such as β-lactamase have been chemically or genetically conjugated to tumor-targeting antibodies and used with β-lactam derivatives of anti-tumor drugs such as cephalosporin mustards and anthracyclines to achieve promising anti-tumor effects in animals. The efficacy of ADEPT is limited, however, by the need for unbound conjugate to clear the circulation before the prodrug can be administered. By the time the circulating conjugate is depleted to the threshold below which systemic activation of the prodrug would produce acceptable levels of toxicity, so much of the conjugate has been lost from the tumor that efficacy is often seriously compromised.

This problem can be overcome by using an interaction-dependent β-lactamase reactivation system with tumor targeting antibodies. When fused to single-chain antibody fragments (scFv) which recognize non-overlapping epitopes on tumor markers, the cis-inhibited β-lactamase and reactivator can localize to the tumor and reconstitute sufficient β-lactamase activity on the tumor cell surface to produce high levels of tumor-localized cytotoxicity from β-lactam prodrugs. The great advantage of such a system is that prodrug activation cannot occur in the general circulation or anywhere the tumor marker is not encountered, so that the prodrug may be administered either simultaneously with high doses of the scFv-fragment fusions, or at the point of highest tumor load of the fragments, without regard for the circulating levels of the fragments which would be completely inactive.

In this example, the construction and purification of fusions of cis-inhibited β-lactamase and reactivator with antibody scFv fragments that bind non-overlapping epitopes on the human breast tumor marker Her-2/neu is described. One may then determine the kinetics of reconstitution of β-lactamase activity on the surface of Her-2/neu—expressing SKBR3 human breast cancer cells. Under conditions of optimum loading, killing of the cells is assessed for different cephalosporin prodrugs as a function of concentrations known to be limiting in vivo. The resulting Tumor-Activated Enzyme Prodrug Therapy (TAcEPT) system is then tested for its ability to ablate SKBR3 and other Her-2/neu-expressing human tumors in severe combined immuno-deficient (scid) mice. Once the efficacy and safety of the system has been demonstrated in animal models, toxicity and efficacy trials are initiated in human breast cancer subjects.

a. Expression of BLIP-D49A-β-Lactamase Fusion and BLIP-142A Reactivator as Fusions to scFv Against Non-Overlapping Epitopes on the Her-2/neu Human Breast Tumor Marker.

The tumor activation mechanism for these components employ two scFvs such as those described by Schier et al. (1996, Gene 169: 147-155), which were derived from a phage display library of a human non-immune repertoire (Marks et al. (1991) J. Mol. Biol. 222: 581-597) by panning against a recombinant fragment comprising the extra-cellular domain (ED) of Her-2/neu. These two scFv appear to recognize non-overlapping epitopes, since they do not compete for binding to the Her-2/neuED by ELISA. The affinity of one of these scFv was improved to sub-nM $K_d$ in vitro (Schier et al. (1996), Gene 169: 147-155), and similar improvements in the other could be made using the same methods (Balint and Larrick (1993) Gene 137: 109-118). The coding sequences for the scFv are subcloned for expression of the scFv as fusions via $(Gly_4Ser)_3$ linkers to the amino termini of the BLIP-D49A-β-lactamase fusion, and BLIP-F142A, respectively. Appropriate vectors are derived from pET26b (Novagen, Inc., Madison, Wis.), and have convenient restriction sites for insertion of both scFv, β-lactamase, and the BLIP coding sequences.

The expression of each fusion protein is fully induced with 1 mM IPTG from the bacteriophage T7 promoter (Moffatt and Studier (1986) J. Mol. Biol. 189: 113-130) under the control of the lac repressor. Each primary translation product contains a pe1B signal peptide for secretion into the bacterial periplasm and a carboxyl-terminal $His_6$ tag for one-step purification from non-denatured lysates (e.g., osmotic shock; (Neu and Heppel (1965) J Biol Chem 240: 3685-92) by IMAC. The yield of each fusion protein can be optimized primarily by manipulation of the inducer concentration and the growth temperature. The purified fusion proteins are tested for binding to an immobilized recombinant fusion of the Her-2/neu extra-cellular domain (ED) to a stabilizing immunoglobulin domain (Ig) by ELISA using an anti-$His_6$ tag antibody (Qiagen). $His_6$-tagged Her-2/neu—Ig fusion may, like the fusion proteins be purified by IMAC, and immobilized on the surface of microtiter plate wells.

b. Determination of the Kinetics of Specific β-Lactamase Activation by Binding of the scFv Fusions to Immobilized Recombinant Antigen.

One may determine β-lactamase activity quantitatively as a function of binding of the fusion proteins to the immobilized recombinant antigen. This rate is then be compared to that obtainable with intact β-lactamase fused to the same scFv as an indication of how much activity may be localized on a tumor compared to the established vehicle, i.e., an antibody-β-lactamase conjugate. First, conditions are established for saturating the antigen with one of the scFv fusion proteins. The wells of microtiter plates are coated with antigen, and exposed to increasing amounts of the first scFv fusion until the ELISA signal plateaus. At this level the antigen is saturated with the first scFv fusion protein, and increasing amounts of the second scFv fusion are added. After binding and washing, β-lactamase activity is determined spectrophotometrically after a 30' incubation with excess (e.g., ~1 mM) nitrocefin (λmax=485 nm; ε=17, 420 M−1 cm−1; McManus-Munoz and Crowder, 1999). Immobilized BSA may be used as the negative control.

If the assay is performed in triplicate, $V_{max}$ is a more or less linear function of the concentration of the second scFv fusion. As the amount of second scFv fusion is increased, at some point $V_{max}$ should plateau. The amount of the second fusion bound can be determined by ELISA, and a relative specific activity ($k_{cat}^{rel}$) may be computed for the reactivated β-lactamase. The $K_M$ may be estimated in solution with saturating antigen and saturating first scFv fusion and limiting amounts of the second scFv fusion. A range of nitrocefin concentrations is added and the initial rates of change of absorbance at 485 nm is measured as a function of second scFv fusion concentration. The $K_M$ is then computed from data by standard regression analysis.

To compare with intact β-lactamase, a fusion of intact β-lactamase to the second scFv may be prepared. This is then added in increasing amounts to antigen-coated wells which had been saturated with the first scFv fusion as had been done before. Again, $V_{max}$ should be a more or less linear function of the amount of intact β-lactamase fusion and should plateau at saturation. At each point, the amount of intact β-lactamase fusion bound, as determined by ELISA, should be comparable to the amount of the second fragment fusion bound, and the ratio of $V_{max}$ should reflect the ratio of specific activities of the intact and fragment-reconstituted β-lactamases. For comparison, the $K_M$ should be estimated as described above for the reactivated enzyme. The reactivated β-lactamase is expected to have a maximum activity ($k_{cat}$) near that of the free enzyme because the BLIP-D49A-β-lactamase complex is under strain with the 15-mer linker, and the affinity of the complex is at least 10-fold lower than that of BLIP-F142A for α-lactamase. If the $K_M$ of reactivated and free β-lactamase are also comparable, activity on a tumor is up to 100-fold higher at the peak of prodrug activation than with the conventional antibody-α-lactamase fusion, which may have 1% or less of its peak activity left when the unbound fusion has cleared the circulation enough to allow prodrug administration.

c. Determination of Killing Kinetics of Her-2/neu-Expressing SKBR3 Ovarian Carcinoma Cells by Tumor-Bound β-Lactamase Activation of Cephalosporin Prodrugs.

Figure 14:
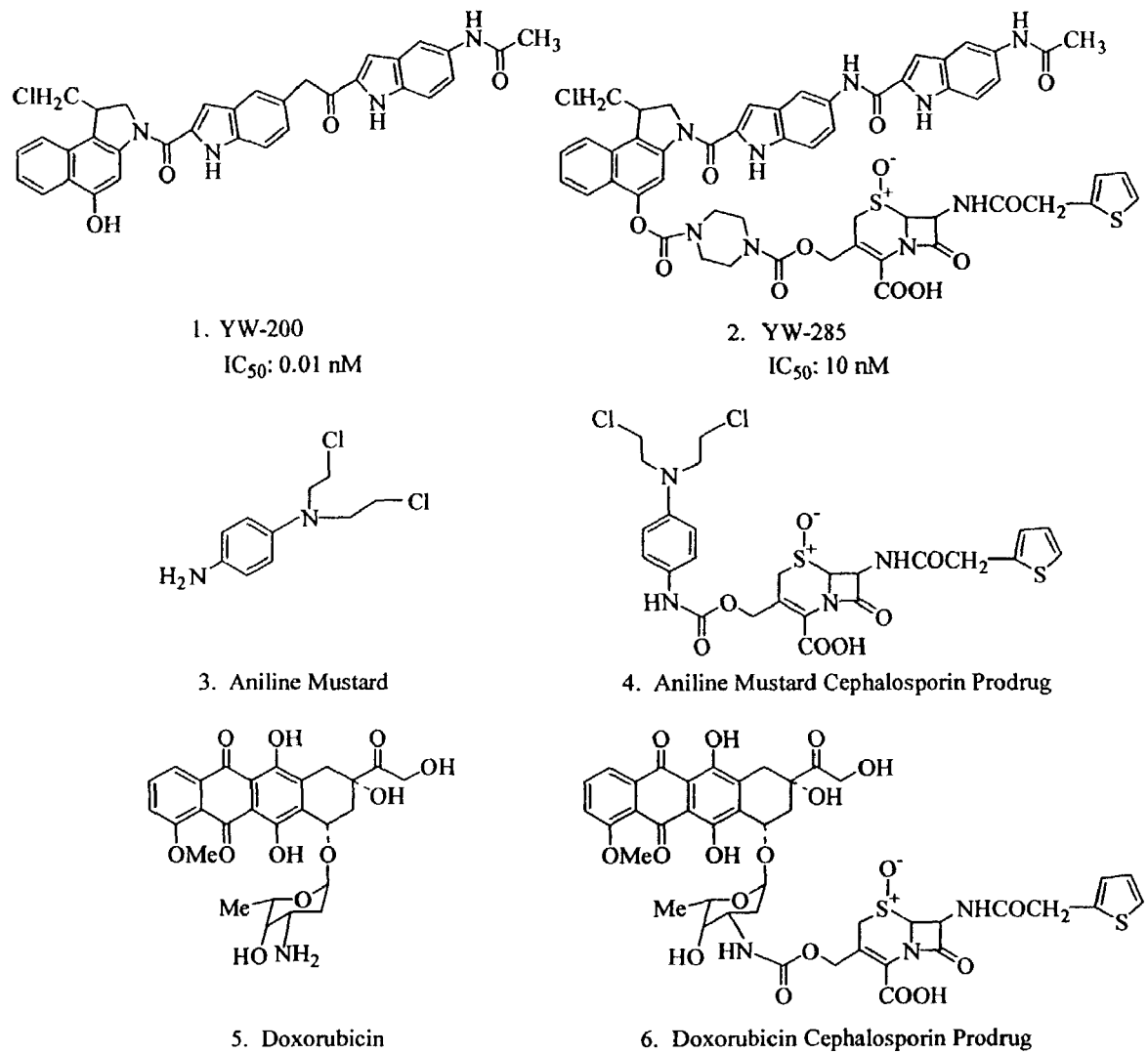
FIG. 14 depicts structures of some anti-cancer drugs and their cephalosporin prodrugs. YW-200 is a DNA-binding tri-indole (Wang et al. (1998) U.S. Pat. No. 5,843,937), and YW-285 is its cephalosporin prodrug. The compounds on the right can be hydrolyzed by β-lactamase to yield the cytotoxic compounds on the left.

The optimized fusions of anti-Her-2/new scFv with β-lactamase reactivation components may then be tested for activation of β-lactamase activity in the presence of human tumor cells expressing the Her-2/neu antigen. Cell killing may be assayed using any of the three cephalosporin prodrugs shown in FIG. 14. The reactivated β-lactamase activity may again be compared with the free β-lactamase activity, this time with respect to tumor cell killing. Such results should indicate the dose range which may be required to show a significant anti-tumor effect in animals, which will be the next step in preclinical evaluation of the tumor-targeted β-lactamase. The SK-BR-3 line of human breast adenocarcinoma cells (ATCC) may be seeded in 6-well tissue culture plates at $3\times10^5$ cells per well in Dulbecco's Minimum Essential Medium (DMEM) supplemented with 10% fetal calf serum (FCS), and allowed to grow to confluency at 37° C. in 10% $CO_2$. The saturability of both Her-2/neu epitopes on the cells may be determined with increasing amounts of intact β-lactamase fused to each scFv, as determined spectrophotometrically after nitrocefin hydrolysis. The $V_{max}$ of the reactivated, cis-inhibited enzyme may then be determined on the cells with saturating concentrations of both scFv fusions and nitrocefin.

$V_{max}$ is expected to conform to the predicted activity based on the maximum uninhibited β-lactamase activity and the ratio of $V_{max}$ observed on the immobilized recombinant antigen. The sensitivity of the cells to any of the three prodrugs shown in FIG. 14 may be determined essentially as described by Marais et al. (1996, *Cancer Research* 56, 4735-42) with and without the uninhibited β-lactamase— scFv fusions and the cis-inhibited β-lactamase reactivation component-scFv fusions under saturating conditions. The prodrugs are dissolved in DMSO and diluted into DMEM/ FCS to a range of concentrations immediately prior to use. One ml is added to each well and the cells are incubated overnight. The cells are then washed, trypsinized, and viability is determined by dye exclusion. Aliquots are then seeded into fresh dishes. After four days of growth, cell viability is assessed by incorporation of [$^3$H] thymidine as determined by liquid scintillation counting of acid insoluble material. The results are expressed as percentage of untreated control cells. Again, the relative cytotoxicities of the prodrugs with the β-lactamase fragment system may be compared to those of the uninhibited β-lactamase fusions, particularly at the lower prodrug concentrations where second order rate constants ($k_{cat}/K_M$) may be important, to give an indication of the potential increase in efficacy of TAcEPT over conventional ADEPT in vivo.

All publications, patents, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting an interaction of binding ensemble members, comprising the steps of:
    providing a responder complex comprising linked components: a responder molecule, an inhibitor of the responder molecule, and a first member of a binding ensemble;
    providing a reactivator complex comprising a reactivator molecule linked to a second member of the binding ensemble;
    combining the responder complex and the reactivator complex, where upon the interaction of the first and the second binding ensemble member, the reactivator competitively or allosterically displaces the inhibitor from the responder molecule; and
    detecting an activity of the responder molecule, thereby detecting the interaction of the first and the second binding ensemble members.

2. The method of claim 1, wherein the first member of the binding ensemble is linked to the responder molecule and the inhibitor is linked to the responder molecule.

3. The method of claim 2, wherein the first member of the binding ensemble and the responder molecule are linked by a first covalent linkage; the inhibitor and the responder molecule are linked by a second covalent linkage; and further, wherein the reactivator and the second member of the binding ensemble by a third covalent linkage.

4. The method of claim 2, wherein the first member of the binding ensemble is a member of a plurality of candidate binding ensemble members.

5. The method of claim 2, wherein the second member of the binding ensemble is a member of a plurality of candidate binding ensemble members.

6. The method of claim 2, further comprising a third member of the binding ensemble, wherein the first member of the binding ensemble and the second member of the binding ensemble interact with the third member of the binding ensemble.

7. The method of claim 6, wherein the third member of the binding ensemble is a member of a plurality of candidate binding ensemble members.

8. The method of claim 6, wherein the first member of the binding ensemble is a member of a plurality of candidate binding ensemble members.

9. The method of claim 6, wherein the second member of the binding ensemble is a member of a plurality of candidate binding ensemble members.

10. The method of claim 6, wherein the third member of the binding ensemble is a member of a plurality of candidate binding ensemble members; the first member of the binding ensemble is a member of a plurality of candidate binding ensemble members; and the second member of the binding ensemble is a member of a plurality of candidate binding ensemble members.

11. The method of claim 1, wherein the responder molecule is linked to the first member of the binding ensemble, and the inhibitor is linked to the first member of the binding ensemble.

12. The method of claim 11, wherein the first member of the binding ensemble and the responder molecule are linked by a first covalent linkage, the inhibitor and the first member of the binding ensemble are linked by a second covalent linkage; and further, wherein the reactivator and the second member of the binding ensemble are linked by a third covalent linkage.

13. The method of claim 12, wherein the first member of the binding ensemble is a member of a plurality of candidate binding ensemble members.

14. The method of claim 12, wherein the second member of the binding ensemble is a member of a plurality of candidate binding ensemble members.

15. The method of claim 12, further comprising a third member of the binding ensemble, wherein the first member of the binding ensemble and the second member of the binding ensemble interact with the third member of the binding ensemble.

16. The method of claim 15, wherein the third member of the binding ensemble is a member of a plurality of candidate binding ensemble members.

17. The method of claim 15, wherein the first member of the binding ensemble is a member of a plurality of candidate binding ensemble members.

18. The method of claim 15, wherein the second member of the binding ensemble is a member of a plurality of candidate binding ensemble members.

19. The method of claim 15, wherein the third member of the binding ensemble is a member of a plurality of candidate binding ensemble members; and further, wherein the first member of the binding ensemble is a member of a plurality of candidate binding ensemble members and the second member of the binding ensemble is a member of a plurality of candidate binding ensemble members.

20. The method of claim 1, wherein the responder molecule is linked to the inhibitor, and the first member of the binding ensemble is linked to the inhibitor.

21. The method of claim 20, wherein the responder molecule and the inhibitor are linked by a first covalent linkage, the first member of the binding ensemble and the inhibitor are linked by a second covalent linkage, and further, wherein the reactivator and the second member of the binding ensemble are linked by a third covalent linkage.

22. The method of claim 20, wherein the responder molecule and the inhibitor are linked by a non-covalent linkage, the first member of the binding ensemble and the inhibitor are linked by a covalent linkage, and further, wherein the reactivator and the second member of the binding ensemble are linked by a covalent linkage.

23. The method of claim 21, wherein the first member of the binding ensemble is a member of a plurality of candidate binding ensemble members.

24. The method of claim 21, wherein the second member of the binding ensemble is a member of a plurality of candidate binding ensemble members.

25. The method of claim 21, further comprising a third member of the binding ensemble, wherein the first member of the binding ensemble and the second member of the binding ensemble interact with the third member of the binding ensemble.

26. The method of claim 25, wherein the third member of the binding ensemble is a member of a plurality of candidate binding ensemble members.

27. The method of claim 25, wherein the first member of the binding ensemble is a member of a plurality of candidate binding ensemble members.

28. The method of claim 25, wherein the second member of the binding ensemble is a member of a plurality of candidate binding ensemble members.

29. The method of claim 25, wherein the third member of the binding ensemble is a member of a plurality of candidate binding ensemble members; and further, wherein the first member of the binding ensemble is a member of a plurality of candidate binding ensemble members and the second member of the binding ensemble is a member of a plurality of candidate binding ensemble members.

* * * * *